US011950893B2

United States Patent
Rudin et al.

(10) Patent No.: US 11,950,893 B2
(45) Date of Patent: Apr. 9, 2024

(54) APPARATUS AND METHOD OF DETERMINING DYNAMIC VASCULAR PARAMETERS OF BLOOD FLOW

(71) Applicants: The Research Foundation for the State University of New York, Amherst, NY (US); CANON MEDICAL SYSTEMS CORPORATION, Otawara (JP)

(72) Inventors: Stephen Rudin, Williamsville, NY (US); Eugene A. Mensah, Tustin, CA (US); Andrew Kuhls-Gilcrist, Tustin, CA (US)

(73) Assignees: The Research Foundation for the State University of New York, Amherst, NY (US); CANON MEDICAL SYSTEMS CORPORATION, Otawara (JP)

(*) Notice: Subject to any disclaimer, the term of this patent is extended or adjusted under 35 U.S.C. 154(b) by 382 days.

(21) Appl. No.: 16/795,469

(22) Filed: Feb. 19, 2020

(65) Prior Publication Data
US 2021/0219849 A1 Jul. 22, 2021

Related U.S. Application Data

(60) Provisional application No. 62/962,689, filed on Jan. 17, 2020.

(51) Int. Cl.
*A61B 5/026* (2006.01)
*A61B 5/021* (2006.01)
(Continued)

(52) U.S. Cl.
CPC .......... *A61B 5/026* (2013.01); *A61B 5/02125* (2013.01); *G06T 7/0012* (2013.01);
(Continued)

(58) Field of Classification Search
CPC ... A61B 5/026; A61B 5/02125; A61B 5/0036; A61B 6/481; A61B 6/032; A61B 5/0275;
(Continued)

(56) References Cited

U.S. PATENT DOCUMENTS

| | | | |
|---|---|---|---|
| 5,186,922 A * | 2/1993 | Shell | A61K 9/1658 424/9.4 |
| 9,082,211 B2 * | 7/2015 | Prevrhal | G06T 11/005 |

(Continued)

FOREIGN PATENT DOCUMENTS

| | | |
|---|---|---|
| EP | 3 403 582 A1 | 11/2018 |
| WO | WO 2008/122971 A1 | 10/2008 |
| WO | WO 2011/091300 A2 | 7/2011 |

OTHER PUBLICATIONS

Elodie Parzy, Sylvain Miraux, Jean-Michel Franconi, and Eric Thiaudiere. "In vivo quantification of blood velocity in mouse carotid and pulmonary arteries by ECG-triggered 3D time-resolved magnetic resonance angiography." Published online in Wiley InterScience: Jan. 20, 2009. (www.interscience.wiley.com) DOI:10.1002/nbm.1365.

*Primary Examiner* — Wesley J Tucker
(74) *Attorney, Agent, or Firm* — Oblon, McClelland, Maier & Neustadt, L.L.P.

(57) ABSTRACT

The present disclosure relates to a method for vascular imaging and determining dynamic vascular parameters of blood flow. According to an embodiment, the present disclosure relates to an apparatus and method of determining dynamic vascular parameters of blood flow, comprising acquiring two-dimensional projection images of a vascular region of interest at a predetermined frequency, the vascular region of interest being downstream of a site of vascular administration of a radio-opaque medium, identifying, within the acquired two-dimensional projection images, heterogeneities of the radio-opaque medium, and determin-
(Continued)

ing the dynamic vascular parameters of the blood flow based on spatial movements of the identified heterogeneities of the radio-opaque medium. In an embodiment, the predetermined frequency is greater than 100 Hz.

17 Claims, 18 Drawing Sheets

(51) Int. Cl.
*G06T 7/00* (2017.01)
*G06T 11/00* (2006.01)

(52) U.S. Cl.
CPC .. *G06T 11/003* (2013.01); *G06T 2207/30048* (2013.01); *G06T 2207/30104* (2013.01); *G06T 2211/404* (2013.01)

(58) Field of Classification Search
CPC ....... A61B 5/7292; A61B 6/507; A61B 6/583; A61B 5/0285; A61B 6/541; G06T 7/0012; G06T 11/003; G06T 2207/30048; G06T 2207/30104; G06T 2211/404; G06T 11/008
See application file for complete search history.

(56) References Cited

U.S. PATENT DOCUMENTS

| | | | | |
|---|---|---|---|---|
| 10,076,301 | B2* | 9/2018 | Millett | A61B 8/12 |
| 10,674,986 | B2* | 6/2020 | Venugopal | A61B 6/032 |
| 11,199,604 | B2* | 12/2021 | Helle | G01R 33/543 |
| 11,471,058 | B2* | 10/2022 | Kang | G06T 7/0012 |
| 2006/0036167 | A1 | 2/2006 | Shina | |
| 2008/0319309 | A1* | 12/2008 | Bredno | A61M 5/007 |
| | | | | 600/431 |
| 2009/0016483 | A1* | 1/2009 | Kawasaki | A61B 6/504 |
| | | | | 378/4 |
| 2012/0243761 | A1* | 9/2012 | Senzig | G16H 50/30 |
| | | | | 378/19 |
| 2013/0237815 | A1* | 9/2013 | Klingenbeck | A61B 6/4014 |
| | | | | 600/431 |
| 2014/0121513 | A1* | 5/2014 | Tolkowsky | G16H 50/30 |
| | | | | 600/431 |
| 2015/0157238 | A1* | 6/2015 | Edelman | A61B 5/318 |
| | | | | 600/413 |
| 2016/0158431 | A1* | 6/2016 | Solem | A61M 1/3656 |
| | | | | 702/140 |
| 2018/0296103 | A1* | 10/2018 | Rege | A61B 5/7207 |
| 2018/0330507 | A1* | 11/2018 | Schormans | G06T 7/0016 |
| 2020/0085396 | A1* | 3/2020 | Song | A61B 6/5217 |
| 2021/0145390 | A1* | 5/2021 | Liu | G06T 7/0016 |
| 2021/0228171 | A1* | 7/2021 | So | A61B 6/504 |
| 2021/0236000 | A1* | 8/2021 | Huo | A61B 5/0044 |
| 2021/0386389 | A1* | 12/2021 | Freiman | G06N 3/08 |
| 2022/0031270 | A1* | 2/2022 | Cohen | A61B 6/5235 |

* cited by examiner

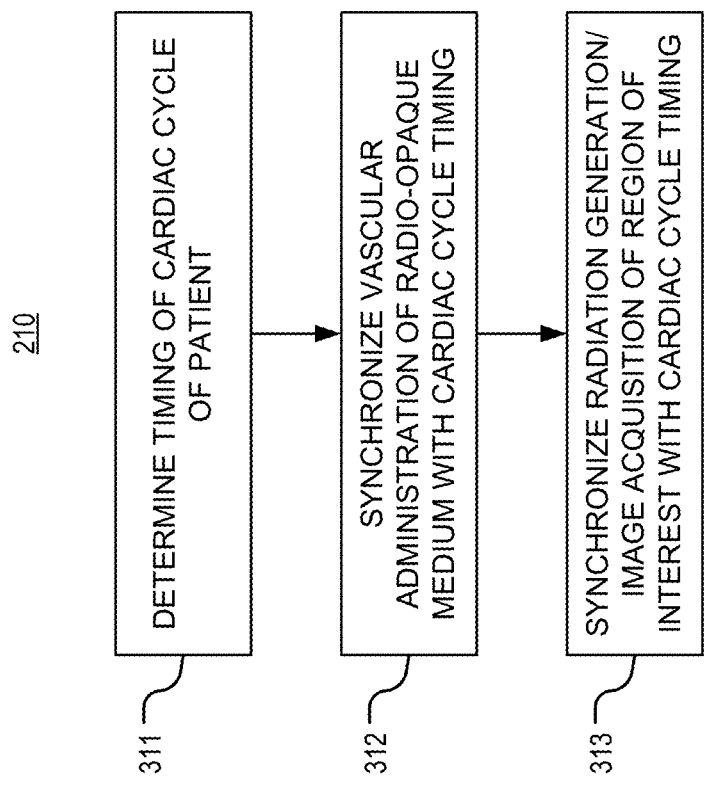

APPARATUS AND METHOD OF DETERMINING DYNAMIC VASCULAR PARAMETERS OF BLOOD FLOW

CROSS-REFERENCE TO RELATED APPLICATIONS

The present application claims priority to U.S. Provisional Application No. 62/962,689, filed Jan. 17, 2020, the teaching of which is incorporated by reference herein in its entirety for all purposes.

STATEMENT REGARDING PRIOR DISCLOSURE BY THE INVENTORS

Aspects of this technology are described in an article "Rapid sequence angiography with a 3D printed aneurysm phantom and an ultra-high frame rate imaging photon counting detector (PCD)", published in Proc. SPIE 10953, Medical Imaging 2019: Biomedical Applications in Molecular, Structural, and Functional Imaging, on Mar. 15, 2019, which is incorporated herein by reference in its entirety.

Aspects of this technology are described in an article "Flow-Pattern Details in an Aneurysm Model Using High-Speed 100-Frames-per-Second Angiography", published in American Journal of Neuroradiology, on Jun. 6, 2019, which is incorporated herein by reference in its entirety.

STATEMENT REGARDING GOVERNMENT SUPPORT

This invention was made with government support under R01EB002873 awarded by National Institutes of Health. The government has certain rights to the invention.

BACKGROUND

Field of the Disclosure

The present disclosure relates to vascular imaging of flow dynamics in the diagnosis, progression, and treatment of neurovascular and cardiovascular pathologies.

Description of the Related Art

Hemodynamics is important in determining intervention outcomes for the millions of people suffering vascular diseases such as cerebrovascular disease and cardiovascular disease. Cerebrovascular disease, for instance, is a leading cause of serious long-term disability in the United States and the second leading cause of death worldwide. Understanding the effects of disturbed blood flow due to vascular disorders can provide insight into the role of complex flow patterns in the development of vascular disease states such as aneurysms and stenosis.

Vascular flow velocities in the human body can be in the order of 10's of cm/s. In the case of patients with vascular disorders such as aneurysms, arteriovenous malformations, or stenotic vessels with some experiencing stroke, not only flow rates but also flow patterns can be impacted. Aneurysms, for instance, are abnormal outpouchings on arteries and treatment may include the use of flow-diverting stents. Flow diverters induce a modification of blood flow within and around the inflow zone of an aneurysm that leads to gradual intra-aneurysmal thrombosis and healing. During the intervention, clinicians must make critical judgements regarding placement, repositioning, and stacking of flow diverters that will ultimately impact treatment efficacy six months to a year later; thus, a detailed understanding of how flow is altered could critically impact treatment.

To this end, direct visualization of vascular flow by angiography may provide information necessary to understand these pathologies and provide insight as to possible treatment strategies. Direct visualization of detailed vascular flow, however, is difficult with conventional angiography deploying flat panel detectors based on larger pixel sizes of 150-200 µm, indirect detection, energy integration and low frame rate acquisition. In fact, conventional angiography implementing flat panel detectors is hindered by image acquisition rates of fewer than 60 frames per second, maximally, and poor spatial resolution. Further, hardware and software constraints of such a system limit the expansion of these metrics and have led those interested in more resolved information related to vascular flow to rely on computational fluid dynamics in order to understand, for instance, the hemodynamics of intracranial arteries.

Although computational fluid dynamics is excellent for the display of detail in hemodynamics, it is an approximation of flow conditions and requires a long computational time to run the simulations, which significantly limits real-time applicability.

Accordingly, the present disclosure provides a system for acquiring angiographic images at higher frame rates in order to extract additional meaningful flow detail that can be used to characterize flow-dependent disease-states.

The foregoing "Background" description is for the purpose of generally presenting the context of the disclosure. Work of the inventors, to the extent it is described in this background section, as well as aspects of the description which may not otherwise qualify as prior art at the time of filing, are neither expressly or impliedly admitted as prior art against the present invention.

SUMMARY

The present disclosure relates to a system for vascular image of flow dynamics.

According to an embodiment, the present disclosure further relates to a method of determining dynamic vascular parameters of blood flow, comprising acquiring two-dimensional projection images of a vascular region of interest at a predetermined frequency, the vascular region of interest being downstream of a site of vascular administration of a radio-opaque medium, identifying, within the acquired two-dimensional projection images, heterogeneities of the radio-opaque medium, and determining, by processing circuitry, the dynamic vascular parameters of the blood flow based on spatial movements of the identified heterogeneities of the radio-opaque medium.

According to an embodiment, the present disclosure further relates to an apparatus for determining dynamic vascular parameters of blood flow, comprising processing circuitry configured to acquire two-dimensional projection images of a vascular region of interest at a predetermined frequency, the vascular region of interest being downstream of a site of vascular administration of a radio-opaque medium, identify heterogeneities of the radio-opaque medium within the acquired two-dimensional projection images, and determine the dynamic vascular parameters of the blood flow based on spatial movements of the identified heterogeneities of the radio-opaque medium.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein:

FIG. 3A is a flow diagram of a sub process of a method of determining dynamic vascular parameters of blood flow, according to an exemplary embodiment of the present disclosure;

DETAILED DESCRIPTION

Figure 1A:
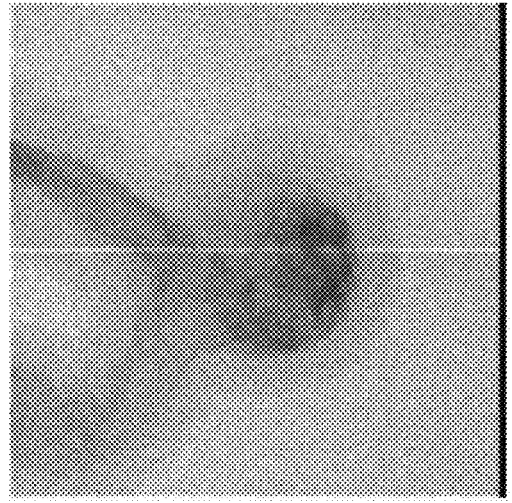
FIG. 1A is an image of an angiographic sequence of vortex flow in an aneurysm, according to an exemplary embodiment of the present disclosure.

The terms "a" or "an", as used herein, are defined as one or more than one. The term "plurality", as used herein, is defined as two or more than two. The term "another", as used herein, is defined as at least a second or more. The terms "including" and/or "having", as used herein, are defined as comprising (i.e., open language). Reference throughout this document to "one embodiment", "certain embodiments". "an embodiment", "an implementation", "an example" or similar terms means that a particular feature, structure, or characteristic described in connection with the embodiment is included in at least one embodiment of the present disclosure. Thus, the appearances of such phrases or in various places throughout this specification are not necessarily all referring to the same embodiment. Furthermore, the particular features, structures, or characteristics may be combined in any suitable manner in one or more embodiments without limitation.

Understanding the effects of disturbed blood flow due to vascular disorders can provide insight into the role of complex flow patterns in the development of vascular disease states. Although widely applicable, particular interest within vascular fluid dynamics has been focused towards areas of stroke due to intracranial neuro-vascular pathologies. These pathologies may consist of ischemia generally due to vessel constrictions or stenosis, hemorrhage generally due to vessel bulges or aneurysms or their potential bursting, and, less frequently, arteriovenous malformations which are analogous to short circuits.

Conventional imaging modalities, however, may not be readily applicable in each of these scenarios. For instance, when these pathologies are intra-cranial, ultrasound is unable to penetrate the skull and thus cannot be used for diagnosis or interventional guidance. Magnetic resonance imaging and computed tomography (CT), though useful for an initial diagnosis, are too slow and physically difficult to use for active guidance during an interventional treatment. In view of the above, the gold standard both for diagnosis and image guidance is X-ray angiography, which can provide general information regarding structures and/or vessel lumens. In certain cases, X-ray angiography can provide average temporal information during bolus injections and follow through of iodine contrast media.

Owing to its limitations, however, angiography is primarily used diagnostically to determine structural problems such as the size and locations of stenotic vessels or the shape and location on the vessel tree of aneurysms and perhaps the feeding vessels for an arteriovenous malformation. It is also importantly used to guide treatments such as the placement of a stent or the filling of an aneurysm with embolic material such as coils generally followed by a binary determination such as whether vessel filling resumes after treatment or if aneurysms are less filled with contrast labeled blood due to a flow diverter stent. Dynamic information regarding details of blood flow, however, particularly any variation during the cardiac cycle, is not commonly determined clinically. Average flow data from time-density curves can provide a group of parameters such as time-to-peak, arrival times, and the like, but their clinical value is unclear. To this end, detailed dynamic flow information such as, for example, streamlines and velocity distributions, are not available during clinical procedures.

Though unavailable at the time of a clinical procedure, such information is viewed as being extremely important in the eventual determination of the success of an interventional procedure as well as the long term clinical outcome for a patient when taken together with other factors.

For example, this type of information can lead to the determination of vessel wall shear stress and other interactions of the detailed blood distribution with the vessel wall and proper alterations during an intervention may be critical for the success of an intervention.

By providing high-speed angiography with detailed information on blood flow and its changes during an interventional procedure, increasingly efficacious treatments with positive outcomes are anticipated. For instance, flow diverters, such as stents, could be selected and repositioned to more accurately modify the blood flow according to the demands of the clinician. Potentially disastrous endoleaks between a device, such as a stent, and the vessel wall could now be accurately assessed and the device guided to eliminate such gaps. Ischemic stroke due to vasospasm after aneurysm rupture may be identified with accurate blood velocity distribution information. Arteriovenous malformations feeder vessels could be better diagnosed and treated by observing the flow timing in detail. Comparisons with predictive computer fluid dynamic calculations could be verified by empirical inpatient flow determinations while the patient is being treated. Changes due to any procedure change may be determined in real-time, thereby avoiding laborious computational efforts.

In an embodiment, and as described above, the apparatus and method of the present disclosure may be considered the standard of care in vascular angiography suites.

In an embodiment, the apparatus and method of the present disclosure may be applied in phantoms and animal studies to determine the impact of medical devices on detailed blood flow and to determine the effect of varying parameters such as device flexure, cardiac cycle, placement accuracy, and deployment methods.

In an embodiment, the apparatus and method of the present disclosure may be applied to applications such as positioning and function of heart valves. The apparatus and method may be beneficial to cardiac applications as the assessment of cardiac motion and blood flow in detail is of high importance, an assessment capability that is presently unavailable.

According to an embodiment, the present disclosure describes an apparatus and method for providing dynamic imaging capabilities presently unavailable to clinicians that improve diagnostic and interventional patient care. The apparatus and method may be applied to real-time vascular imaging to visualize intricate details of blood flow that can be critical in determining clinical procedure outcomes.

According to an embodiment, the present disclosure describes an apparatus and method for providing dynamic imaging capabilities at temporal resolutions of 1 millisecond (ms).

According to an embodiment, the present disclosure describes a high-speed vascular imaging system (HVIS). The HVIS may include a two-dimensional detector. In an example, the HVIS may include biplane 5 cm×7.5 cm field of view (FOV) detectors. An advantage of biplane imaging of sparse objects, such as the vasculature after subtraction of background fixed objects, is the ability to infer three-dimensional information. If the three-dimensional vessel morphology using either multi-slice CT or cone beam CT is acquired prior to a biplane angiographic sequence, it is possible to obtain three-dimensional contrast motion information from the acquired biplane sequences that may better enable depiction of more accurate velocity distributions. In its simplest form, 3D velocities may be determined from identified point-like features in successive biplane images. These results can be validated in 3D models using contrast particles, such as small microspheres impregnated with iodine, using an X-ray particular image velocimetry. Alternatively, droplets of undiluted contrast material such as Ethiodol, air bubbles, or particles of dried iodine contrast will be studied so as to find an X-ray particle image velocimetry-like method that may be more conveniently clinically transferable.

In an embodiment, high-speed 1000 frames per second (fps) detectors may be used to obtain sequences of cone beam CT images at rotation rates of four revolutions per second, much faster than existing cone beam CT scanner systems.

According to an embodiment, the HVIS includes synchronization circuits for triggering X-ray sources for X-ray generation and an injector for contrast medium injection. The injector and associated software may allow delivery of variable volumes, or globs, of contrast medium or contrast labelled particles for X-ray particle image velocimetry. The contrast medium may be a radio-opaque medium and may be selected in order to allow for investigation of flow dynamics via leading edges of flowing contrast.

According to an embodiment, the HVIS may include a flow loop with accurate pressure measurements that may be assembled and connected to a variety of three-dimensional printed flow phantoms. Moreover, the HVIS may include a high-speed vascular cone beam CT scanner implementing detectors that may acquire images at 1000 fps.

According to an embodiment, HVIS may include an evaluation module, or analysis module, for investigating detailed flow patterns. In vitro, the investigations may be performed on three-dimensional printed models of patient specific aneurysms with and without flow diverters. Streamlines and velocity distributions leading to wall shear stress and other measures may be determined and compared quantitatively with computational fluid dynamics (CFD) calculations. Effects of vessel and flow diverter device deformity in three-dimensional models, as well as animal studies, may be investigated. Vascular flow investigations may focus on neurovascular flow and cardiovascular flow. Such investigations may also allow for evaluation of the balance between radiation dose and optimal imaging parameters such as fps, sequence duration, and quantum noise and anatomical noise for different diagnostic and interventional tasks.

According to an embodiment, the present disclosure describes a HVIS implementing image acquisition at 1000 fps in clinical procedure rooms with minimal modifications to the X-ray source, high voltage generation, and detector. For instance, the HVIS may include one or more high-speed detectors.

According to an embodiment, the present disclosure describes a HVIS implementing injection of reproducible non-homogenous (i.e., heterogeneous), globular and/or labeled microspheres for contrast injections. In an embodiment, the HVIS may also include a control module for synchronizing contrast injections with X-ray generation and image acquisition via high-speed detector. In an embodiment, the HVIS may include an analysis module for determining the impact of certain detailed flow imaging parameters, such as fps, sequence duration, dose, optimum X-ray generation parameters, catheter position and motion, vessel and device flexure, and cardiac-like pump timing and pressures, and determining dynamic vascular parameters such as velocity distributions and wall shear stresses which can be compared with and validation for CFD calculations.

According to an embodiment, the present disclosure describes a HVIS implementing gelatin-polymer microsphere particles labeled with iodine for use with X-ray particle image velocimetry in patient specific phantoms using standard X-ray sources.

According to an embodiment, the HVIS may be based on negligibly-low-instrumentation-noise cadmium telluride (CdTe) X-ray detectors. Such detectors enable the innovation of creating a clinical X-ray angiography system to provide detailed patient blood flow using X-ray sources that are essentially unchanged from current commercially available systems. In an embodiment, only timing modifications to provide appropriate system synchronization must be made. In this way, the HVIS represents a new paradigm for X-ray angiography where there is a short duration of continuous X-ray exposure simultaneously with high-speed 1000 fps image acquisition. In an embodiment, the HVIS employs a single plane imaging capability for providing detailed flow information. In an embodiment, the HVIS employs biplane imaging capability and three-dimensional software computations to acquire detailed three-dimensional flow information.

In any event, high-speed detailed flow information may be made available to a clinical specialist in real-time and during treatment of a patient. This eliminates the need to wait for a CFD calculation, which itself may be of limited utility if devices or vessels were to flex or blood pressure change during an intervention.

Figure 1B:
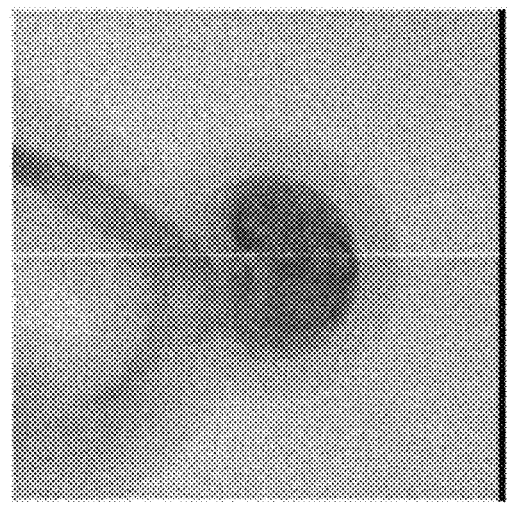
FIG. 1B is an image of an angiographic sequence of vortex flow in an aneurysm, according to an exemplary embodiment of the present disclosure.
Figure 1C:
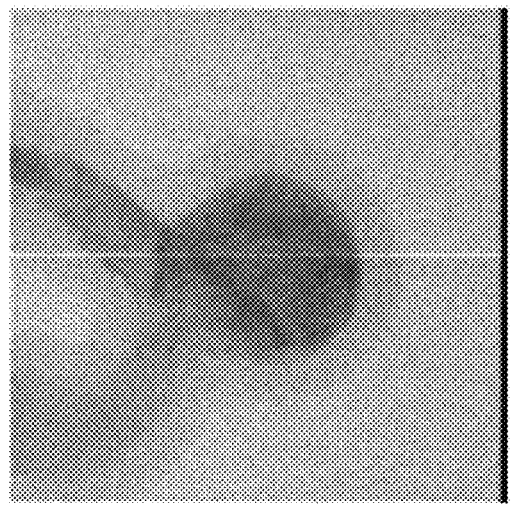
FIG. 1C is an image of an angiographic sequence of vortex flow in an aneurysm, according to an exemplary embodiment of the present disclosure.

Turning now to the Figures, FIG. 1A through FIG. 1C demonstrate images generated by a HVIS implementing a portion or all of the methods described herein. In particular, FIG. 1A through FIG. 1C demonstrate fluid flow through an aneurysm phantom, each image being acquired at 1000 fps and being separated by 25 ms. As can be visually appreciated by the darkened regions within the aneurysm phantom, FIG. 1A demonstrates an initiation of flow while FIG. 1C demonstrates development of a vortex within the aneurysm sac as a result of continued flow. Note that the central vertical white line is a result of two separated detector modules and can be removed by pixel interpolation. In the HVIS, the temporally-acquired series of images may be analyzed to determined fluid flow information of the medium within the fabricated vascular network. Such information may be previously unattainable, limited by conventional methodologies that cannot resolve information within the millisecond. However, the HVIS allows for the capturing of such data and evaluation of the data for flow information including dynamic vascular parameters such as streamlines, velocities, and the like.

The HVIS of FIG. 1A through FIG. 1C, representative of an embodiment of the present disclosure, will now be generally and specifically described throughout the remainder of the text.

Figure 2:
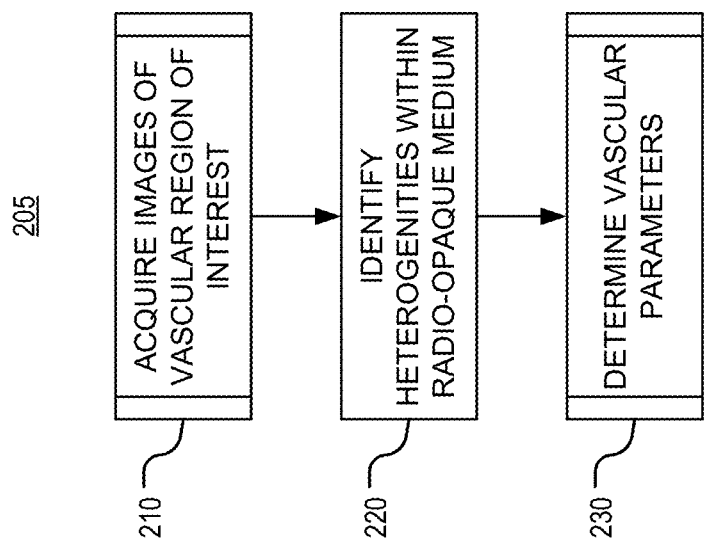
FIG. 2 is a flow diagram of a method of determining dynamic vascular parameters of blood flow, according to an exemplary embodiment of the present disclosure.

With reference to FIG. 2, the method of FIG. 1A through FIG. 1C will now be described. At sub process 210 of method 205, images of a vascular region of interest can be acquired. The images may be temporally-acquired such that serial images are acquired sequentially. In an embodiment, the images may be acquired at rates above 30 fps. In an embodiment, the images may be acquired at rates above 60 fps. In an embodiment, the images are acquired at rates above 100 fps. In an embodiment, the images are acquired at rates equal to or above 1000 fps.

In an embodiment, the images of the vascular region of interest may be acquired by a CdTe single counting-photon detector. In another embodiment, the detector may be a detector having multiple modules providing a FOV of 5 cm×7.5 cm. Such detector may provide a FOV that is 6× larger than other detectors and provide considerably more digital memory with a similar frame rate and charge sharing correction capabilities for accurate pixel localization of detected X-ray photons. In an embodiment, the vascular region of interest may be the site of an aneurysm and the like. The vascular region of interest may be an ischemic site, a heart valve, or other vascular tissue that may benefit from fluid flow analysis. It can be appreciated that initial work may be performed on phantoms of the above-described physiological conditions, though it can be appreciated that the apparatus and methods herein can be implemented within an in vivo system.

In an embodiment, large FOV region of interest detectors may be used in order to image patient-specific three-dimensional printed vascular phantoms. In another embodiment, a single, limited FOV detector may be used. In an embodiment, the HVIS may employ a biplane detector system.

According to an embodiment, the HVIS may include a support structure. A temporary support structure may be constructed to support a phantom, in the case of phantom experiments, and a detector for use with a mobile C-arm. The support structure may be constructed from Unistrut or may be enhanced for use with a different detector configuration such as a biplane configuration. With regard to biplane configurations, a mobile C-arm may be used as a lateral tube rather than a ceiling mounted C-arm which is designed to be triggered alternately to an AP C-arm and hence would not allow the precise simultaneous acquisition needed to observe three-dimensional flow. Descriptions of previous detector supports have been provided both for manual and motorized implementation, as described in Wang W. et al. *New High-Resolution-Detector Changer for a Clinical Fluoroscopic C-Arm Unit* (abstract), Medical Physics, 36(6):2474, June 2009 and Rudin, S. *Part of Session: Advances in Image-Guided Neurointerventions-Clinical Pull and Technology Push* (abstract), Medical Physics, 43(6), June 2016, 2016 AAPM Annual Meeting Program p. 3815-6, each of which are incorporated herein by reference.

In an embodiment, images acquired at sub process 210 of method 205 may be displayed, manipulated, analyzed, and the like, via a display module. The display module may include a control, acquisition, processing, and image display system (CAPIDS).

With reference to sub process 210 of method 205, the vascular region of interest may also be a site immediately downstream from a site of an injection of a contrast medium. The contrast medium may include be a radio-opaque dye. The contrast medium may be air bubbles and the like. The contrast medium may be a colloidal solution of small radio-opaque particles that do not change their physical characteristics in fluid. For example, iodine labeled embospheres or an Ethiodol-like contrast agent (e.g., poppy-seed oil and iodine contrast) may offer a contrast medium with longer lifetime in the vessel model. The contrast medium may be such that a position of particles within the contrast medium can be followed across sequential and temporally-acquired images of the vascular region of interest.

The contrast medium may be provided immediately upstream of the vascular region of interest and may be provided by manual injection or by automated injection. The injection of the contrast medium may be pulsatile and may be synchronized with initiation of radiation generation and/or image acquisition. Regarding automated injection, and with reference to step 220 of method 205, a non-uniform contrast medium, administered as streams, globs, or particles, may be provided in order to allow for tracking of said non-uniformities, or heterogeneities, from image to image. The use of identifiable streams, globs, or particles allows for the evaluation of a 'leading edge' of a bolus of contrast medium, eliminating issues with a region of interest that may be awash with contrast or appear homogenous. The ability to identify and track the heterogeneities of the contrast medium at step 220 of method 205 allows for the determination of fluid flow characteristics. In an embodiment, the automated injection may be pulsatile and may be designed to inject a bolus of contrast medium with a frequency range of between 1 Hz and 20 Hz. In an embodiment, a rotary peristaltic pump capable of providing high frequencies may be employed. Other considerations such as the effect on velocity distribution of the diffusion of the contrast medium may be studied and may require careful calibration of flow modification.

In an embodiment, microspheres with iodine may be used for calibration. The microspheres may be precisely calibrated acrylic polymer microspheres impregnated with porcine gelatin. The microspheres may have a diameter ranging between 40 µm to over 1 mm. Though they may be used for embolic treatments, the microspheres may be soaked in iodine contrast media to label them. Accordingly, as at step 220 of method 205 in an embodiment, images may be obtained wherein the soaked microspheres may be tracked. Other contrast media such as ethiodized oil (Ethiodol), an oily-based media which has been used in arteriovenous malformation clinical procedures, may be used in flow calibrations for laboratory use. Using the HVIS system of the present disclosure, the automated injector will be calibrated and/or synchronized to inject contrast without disrupting blood flow.

At sub process 230 of method 205, the identified heterogeneities can be exploited for determination of vascular parameters including fluid flow information within the vascular region of interest. Such vascular parameters may include velocity distributions and streamlines and will be described in greater detail with respect to FIG. 6.

According to an embodiment, sub process 210 of method 205 may include synchronization of image acquisition, X-ray generation, and contrast medium injection. In an embodiment, the synchronization may be based on a biometric signal of a patient. The biometric signal of the patient may be a cardiac signal such as an electrocardiogram and the like.

As described above, useful flow information is primarily located within an initial 'leading edge' of a contrast medium. Because results primarily originate from a brief period at the beginning of a contrast medium injection where the contrast is not uniform and able to depict flow details, synchronization of all three components of the HVIS, the X-ray source, the detector, and the contrast injector, is critical. Each of the three components may be triggered by programmable delays. The trigger may be based on input from a desired phase of a cardiac cycle derived from an electrocardiogram signal. By synchronizing each aspect of the HVIS, image acquisition can be performed while minimizing patient exposure to harmful radiation. For a biplane configuration, two imaging chains will both have synchronization systems triggered by the same electrocardiogram-derived signal. A synchronization module may execute the synchronization and may utilize a controller area network bus to enable communication between all components of the imaging chain in real-time.

Figure 3B:
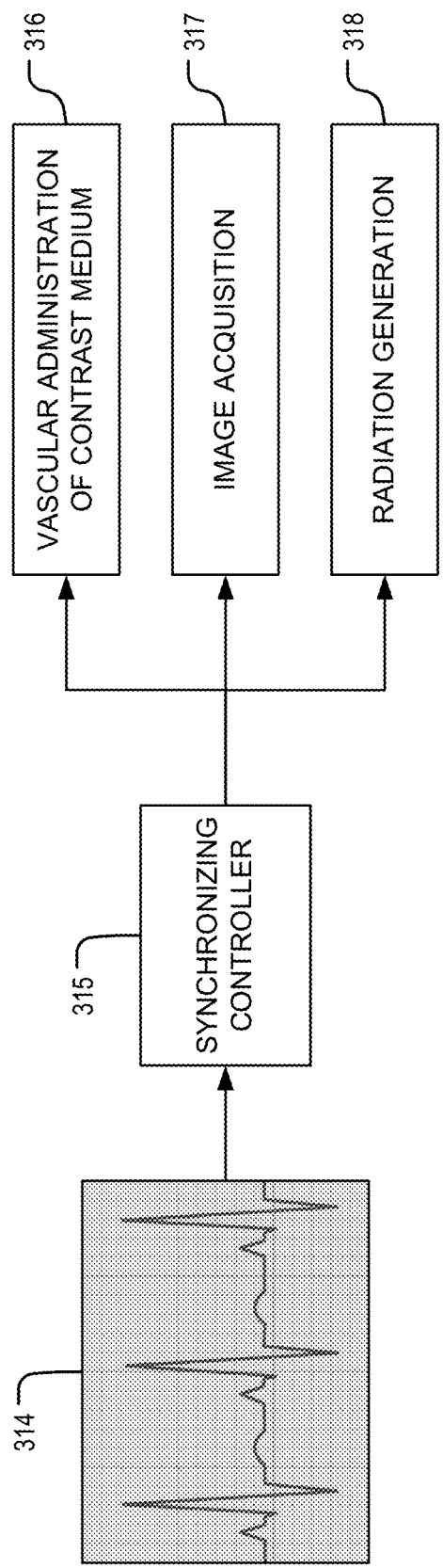
FIG. 3B is a flow diagram of a sub process of a method of determining dynamic vascular parameters of blood flow, according to an exemplary embodiment of the present disclosure.

With reference now to FIG. 3A and FIG. 3B, synchronization, as executed by the synchronization module having a synchronizing controller 315, will be described. At step 311 of sub process 210, timing of a cardiac cycle of a patient can be determined. The cardiac cycle of the patient can be derived from an electrocardiogram 314 of the patient. In an example, the determined timing of the cardiac cycle may indicate a period after contraction of the heart. In another example, the determined timing of the cardiac cycle may indicate a period at the end of the QRS complex.

At step 312 of sub process 210, vascular administration of contrast medium 316 may be synchronized with the determined timing of the cardiac cycle. For instance, the determined timing of the cardiac cycle may be the period after contraction of the heart during which injection of contrast medium should be initiated. In another instance, the determined timing of the cardiac cycle may indicate a period at the end of the QRS complex during which injection of the contrast medium should be initiated. The contrast medium may be, in an example, a radio-opaque medium.

At step 313 of sub process 210, radiation generation 318 and image acquisition 317 may be synchronized with the determined timing of the cardiac cycle and the administration of the contrast medium 316. In an embodiment, a delay may be programmed within the synchronizing controller 315 such that radiation generation 318, or X-ray generation, and image acquisition 317 are performed only when necessary following administration of the contrast medium 316.

Figure 4C:
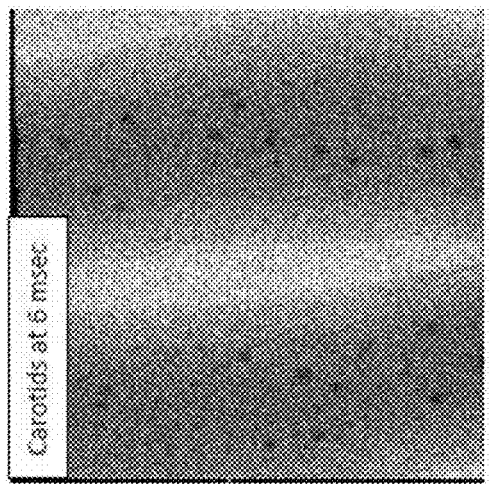
FIG. 4C is an image of contrast agent with a carotid phantom, according to an exemplary embodiment of the present disclosure.
Figure 4B:
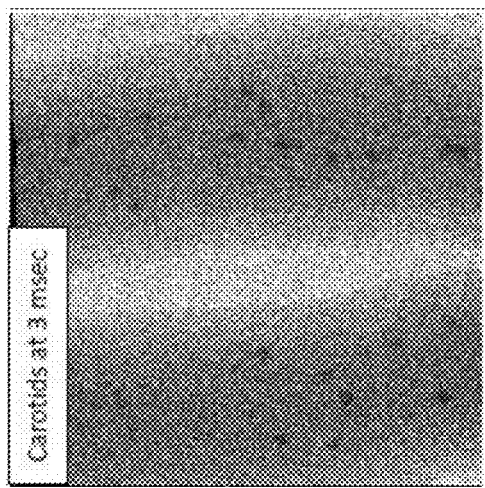
FIG. 4B is an image of contrast agent with a carotid phantom, according to an exemplary embodiment of the present disclosure.
Figure 4A:
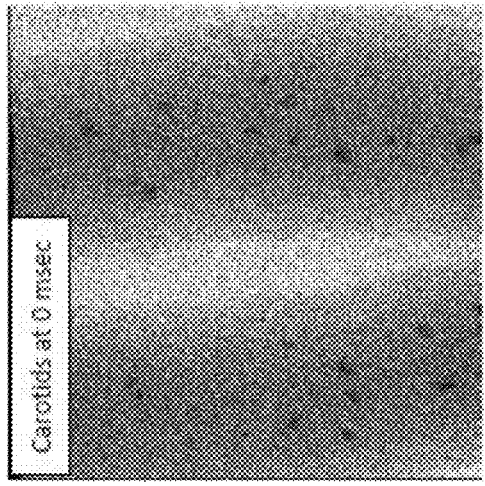
FIG. 4A is an image of contrast agent with a carotid phantom, according to an exemplary embodiment of the present disclosure.

FIG. 4A through FIG. 4C demonstrate tracking of particles within contrast medium across images acquired during 1 ms at 3 ms intervals. The images are of a carotid phantom above the bifurcation where microspheres can be followed from frame to successive frame, allowing the calculation of their velocity and reconstruction of their streamlines. A similar technique using lasers, high-speed cameras, and light scattering particles in a moving fluid is a standard optical technique called particle image velocimetry. According to an embodiment, the HVIS of the present disclosure provides an apparatus and method for X-ray particle image velocimetry and enables quantitative calibration of flow velocity in three-dimensional printed phantoms.

According to an embodiment, the phantoms described herein may be a flow loop with pressure sensors providing accurate pressure measurements. The flow loops may be assembled and connected to any of a variety of three-dimensional printed phantoms such as the Circle of Willis and coronary artery phantoms. In an embodiment, the three-dimensional printing vascular phantoms may be patient-specific and derived from clinical CT angiograms. Additionally, for neurovascular measurements, the vessels in the Circle of Willis may be placed into a skull phantom that has realistic bone details to enable an accurate human phantom when additional plastic scattering material is used.

Figure 5A:
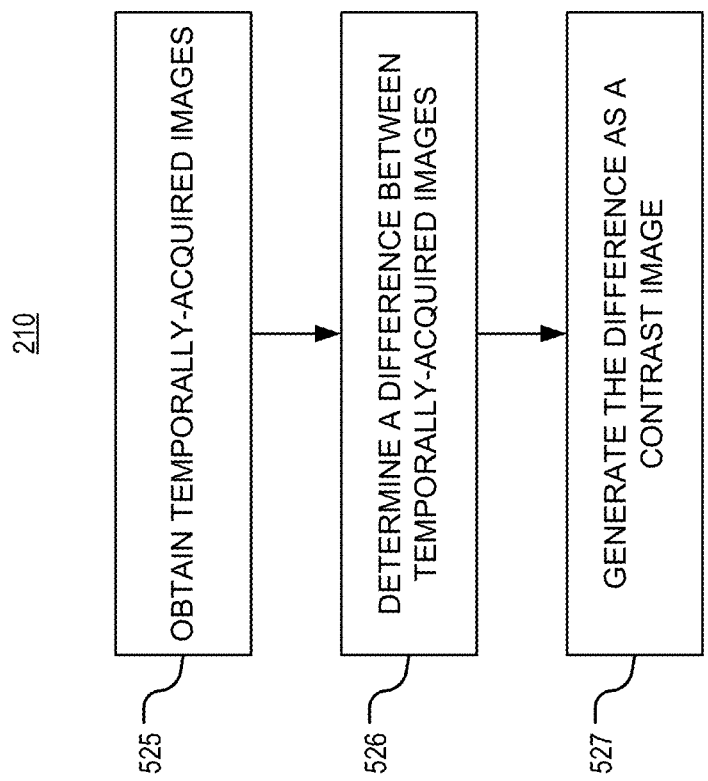
FIG. 5A is a flow diagram of a sub process of a method of determining dynamic vascular parameters of blood flow, according to an exemplary embodiment of the present disclosure.
Figure 5B:
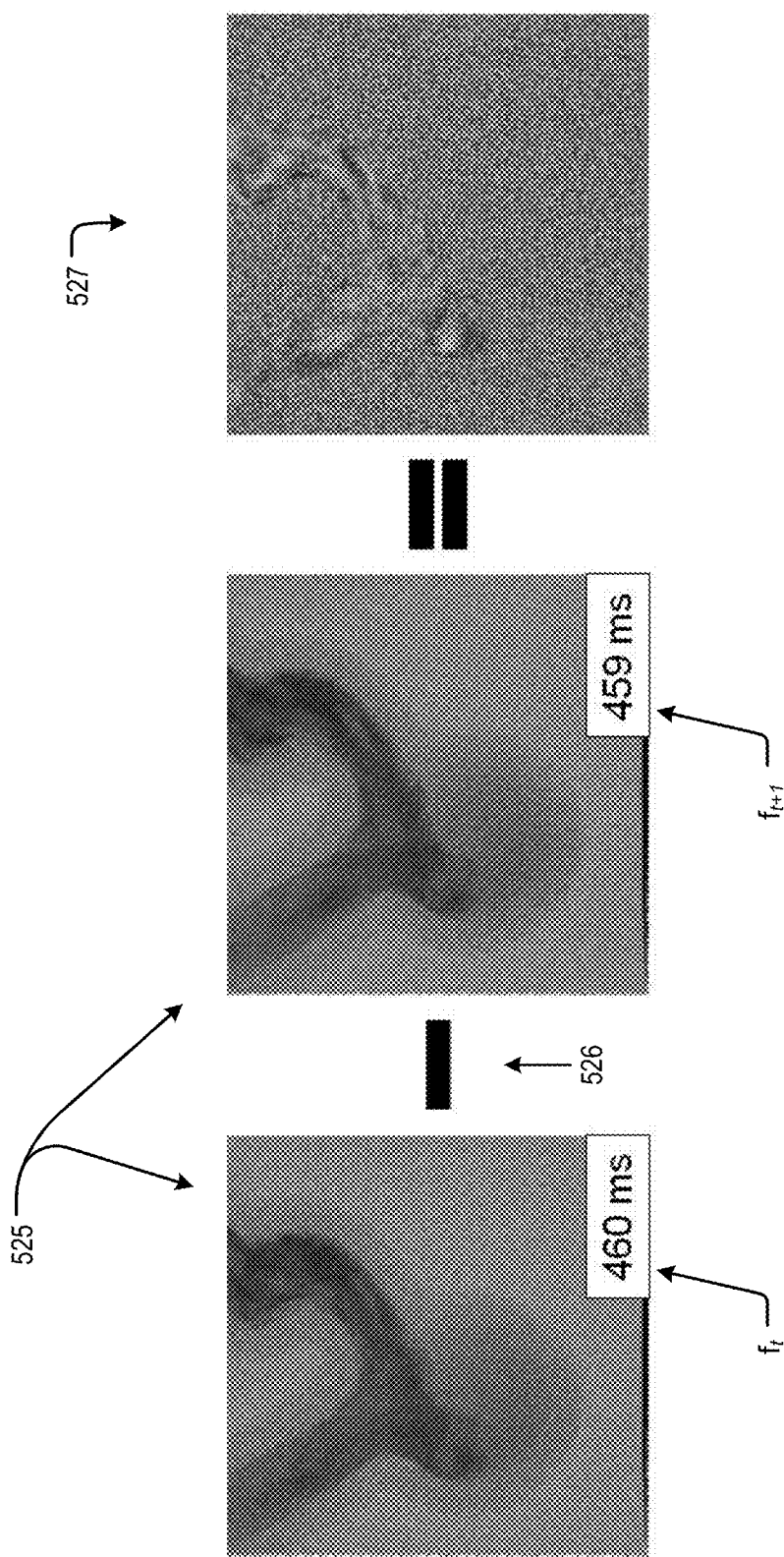
FIG. 5B is an illustration of a sub process of a method of determining dynamic vascular parameters of blood flow, according to an exemplary embodiment of the present disclosure.
Figure 5C:
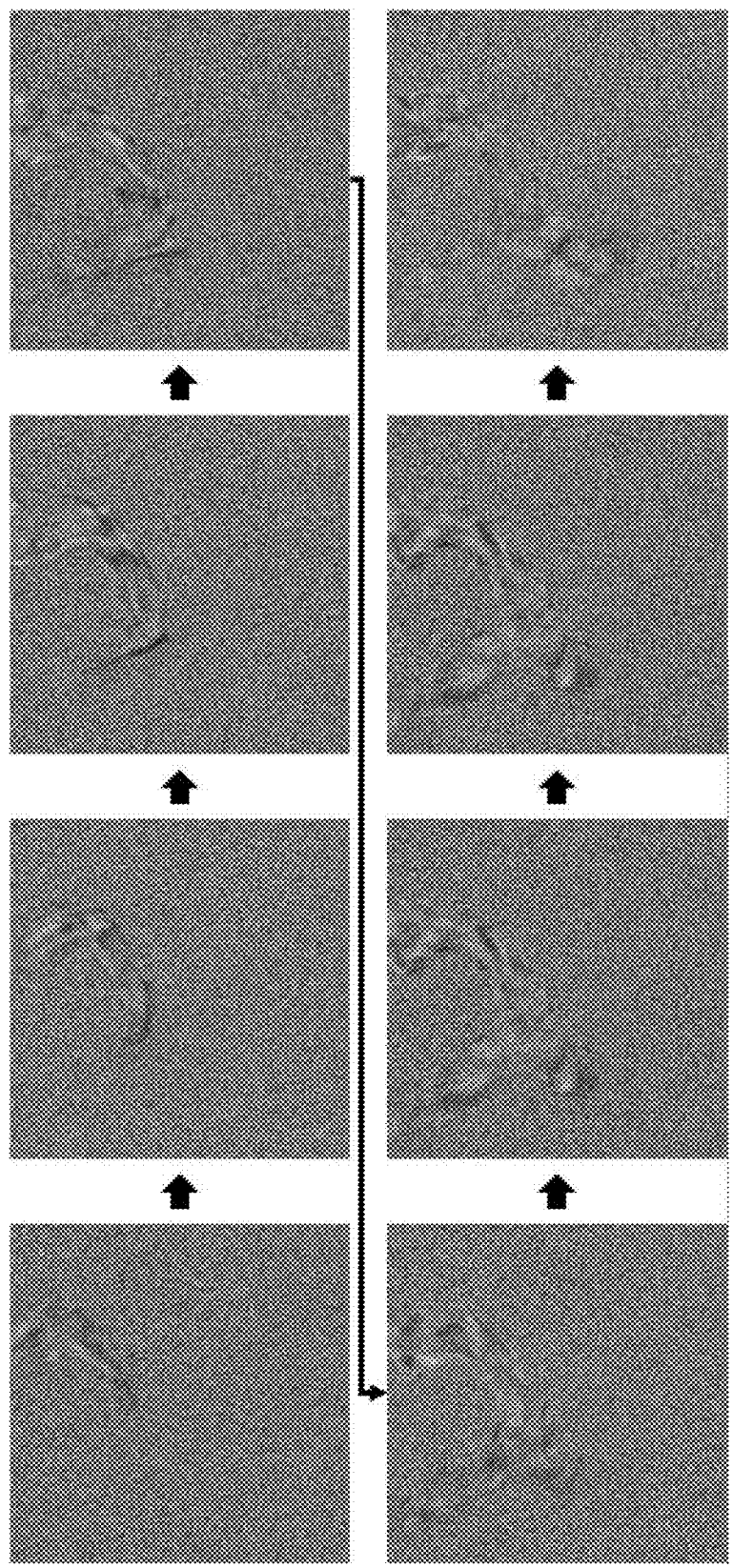
FIG. 5C is an illustration of a step of a sub process of a method of determining dynamic vascular parameters of blood flow, according to an exemplary embodiment of the present disclosure.

With reference now to FIG. 5A, sub process 210 of method 205 will be described according to an exemplary embodiment of the present disclosure. At step 525 of sub process 210, temporally-acquired images may be obtained. A difference between the temporally-acquired images may be obtained at step 526 of sub process 210. The difference may be a digital subtraction of a subsequent image frame from an initial image frame, as shown in FIG. 5B. In FIG. 5B, step 525 of sub process 210 demonstrates obtaining temporally-acquired images of a vascular region of interest. At step 526 of sub process 210, a digital subtraction of the subsequent frame and the initial frame is performed. With reference now to both FIG. 5A and FIG. 5B, the digital subtraction may generate the difference as a contrast image at step 527 of sub process 210. It can be appreciated that the contents of the contrast image at generated at step 527 of sub process 210 reflect changes between an image acquired at $f_{i+1}$, or the acquisition time of the subsequent frame, and $f_i$, or the acquisition time of the initial frame. As in FIG. 5C, a series of contrast images may be calculated for each pair of initial images and subsequent images at step 527 of sub process 210. The series of contrast images may be used in identifying heterogeneities within the region of interest.

For instance, in an embodiment, a center of mass of contrast fronts may be tracked between frames and serve as positional data. The positional data may be used to calculate a velocity of contrast, wherein velocities can be subsequently mapped onto the image.

Figure 6:
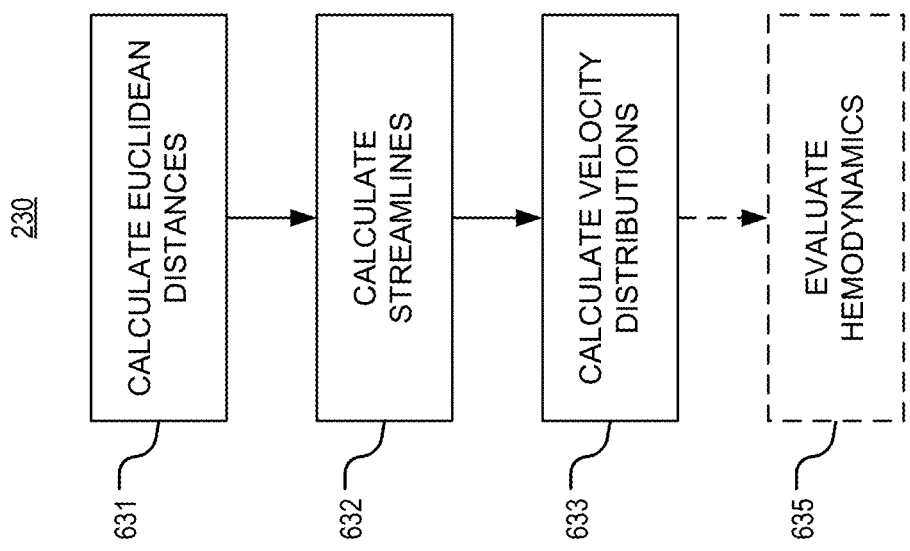
FIG. 6 is a flow diagram of a sub process of a method of determining dynamic vascular parameters of blood flow, according to an exemplary embodiment of the present disclosure.

With reference now to FIG. 6, sub process 230 of method 205 will be described. It can be appreciated that sub process 230 of method 205 can be performed for subsequent images and for a series of images acquired of a vascular region of interest. Positional data can be extracted from identified heterogeneities of contrast images generated at step 210 of method 205 and step 220 of method 205. Euclidean distances between positional data associated with corresponding heterogeneities can be calculated at step 631 of sub process 230. Based on the Euclidean distances, local velocities can be calculated along with streamlines at step 632 of sub process 230 and velocity distributions at step 633 of sub process 230. Velocities may calculated pursuant to Example 1 and the following equation, $$v = \frac{\sqrt{(X_f - X_i)^2 + (Y_f - Y_i)^2}}{1 \text{ ms}} * 100 \text{ μm},$$

where $X_i, Y_i$ and $X_f, Y_f$ reflect pixel coordinates of positional data associated with corresponding heterogeneities across image frames.

Figure 7:
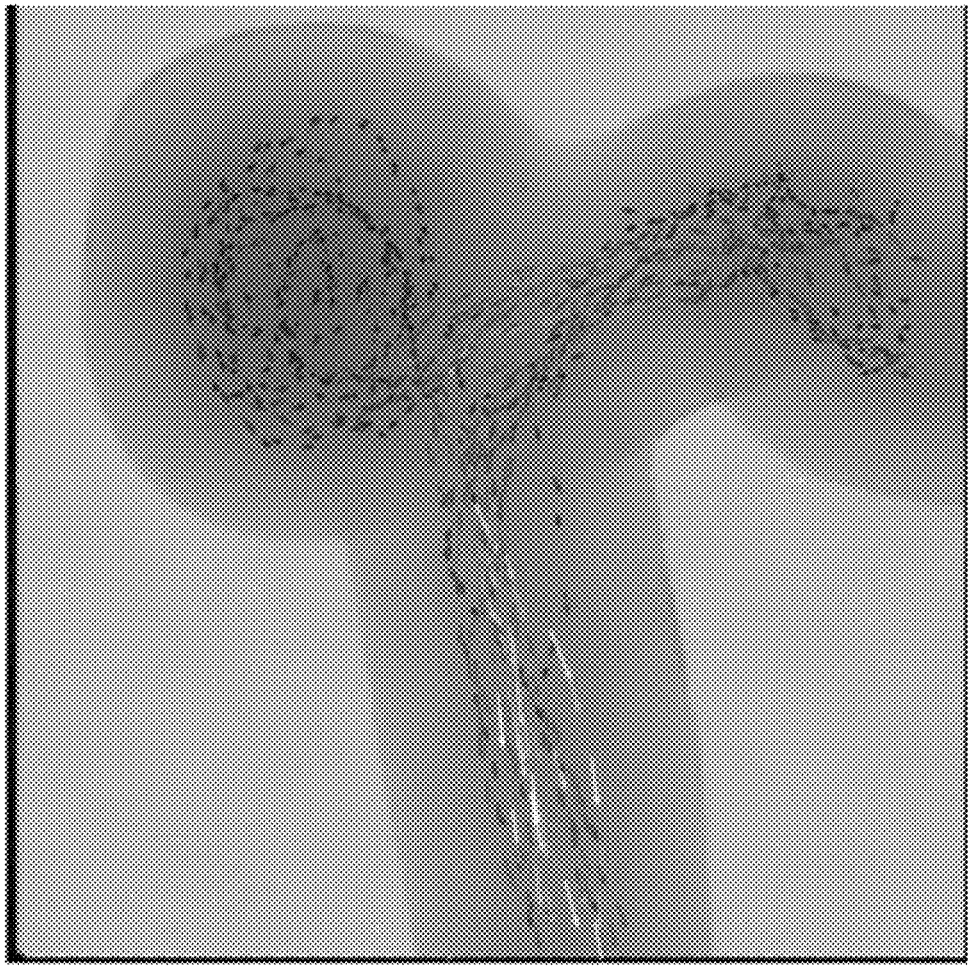
FIG. 7 is an illustration of dynamic vascular parameters of blood flow, according to an exemplary embodiment of the present disclosure.

Variation of flow streamlines will give qualitative and semi-quantitative information and help an observer begin to assess basic flow characteristics such as diversions, divisions at bifurcations, and vorticity in aneurysms. Velocity distributions can be derived from an analysis of image sequences as for local velocities. This may be done by manually following the edge of contrast globs through successive images in a 1000 fps sequence with the length of the velocity arrow being the magnitude and the direction estimated by the observed directional change in an edge feature. In an embodiment, aneurysm velocity data may be acquired from individual frames. FIG. 7 illustrates a velocity distribution as calculated at step 633 of sub process 230. In FIG. 7, each arrow is a vector indicating a direction of flow and, via a length of each arrow, a corresponding velocity of flow at that position. Having calculated a non-limiting subset of vascular parameters at steps 632 and 633 of sub process 230, hemodynamics may be evaluated at step 635. Such evaluation may indicate efficacy of an intervention where fluid velocity distributions are primarily confined along a fluid diverter, for instance, and not within an aneurysm sac.

Wall shear stresses and other dynamic vascular parameters may be calculated from fluid velocity distributions. This is convention when performing CFD calculations. It is understood that these vessel parameters play key roles in the determination of vessel pathology. Usually, however, for CFD calculations, many assumptions such as initial conditions and rigidity of the vessel walls are made and the actual calculations, especially when models of interventional devices are included, can take substantial computer power with results returning to the investigator or interventional clinician in hours or even days. An advantage of the apparatus and method, described herein, for determining velocity distributions, and vessel analysis parameters therefrom, is in enabling clinicians to use such information to modify and improve interventions in real-time intraoperatively.

According to an embodiment, vessels may be somewhat deformed during a procedure as devices are either inserted or deployed, and interventional devices once deployed may be different in shape or location from what was originally planned or assumed in the CFD calculation. The extent of these actual changes may be evaluated in a variety of three-dimensional printed models.

According to an embodiment, the apparatus and methods of the present disclosure may be applied in vivo. To this end, work performed on vasculature of a live rabbit model demonstrated the effect on detailed flow through the aortic valve with subsequent contrast flow down the descending aorta.

According to an embodiment, an application of the HVIS may be assessment of severity of sub-arachnoid hemorrhage (SAH) due to aneurysm rupture. During this very high-mortality high-disability occurrence, the blood in the subarachnoid space acts as an irritant which causes vasospasm. This is known to cause delayed ischemic neurologic injury, and remains the most significant source of morbidity and mortality after intracranial aneurysm rupture. SAH patients undergo surveillance for vasospasm for at least 14 days in the intensive care unit. Surveillance techniques include diagnostic imaging with transcranial Doppler, CT-angiography, and CT-perfusion. Depending on the severity of the spasm and clinical symptoms, various prophylactic and therapeutic interventions are available, including hypertension management, intra-arterial spasmolytics, and angioplasty. Based on transcranial Doppler measurements of the mean velocity for the middle cerebral artery (MCA), the vasospasm can be divided into three levels: mild, moderate or severe. Mild diagnosis has velocities in the range of 0-119 cm/s, with a literature-reported mean of 62±12 cm/s with no neurological changes. Moderate spasm corresponds to an MCA mean velocity of 120-199 cm/s with no neurological changes. Severe spasm is marked by mean velocities above 200 cm/s or new neurological deficit. Transcranial Doppler, however, generally cannot be performed during endovascular procedures and it has some limitations including: operator dependence, requires a good acoustic window, has low sensitivity, can be falsely positive with induced hypertension, may have poor correlation with cerebral angiography in the anterior cerebral artery territory, and poorly reflects smaller vessel vasospasm compared with perfusion imaging. Nearly all patients undergo angiography at the time of initial presentation after SAH. Therefore, quantitative angiography using the HVIS of the present disclosure may prove useful in early detection and triage of these patients.

Figure 8:
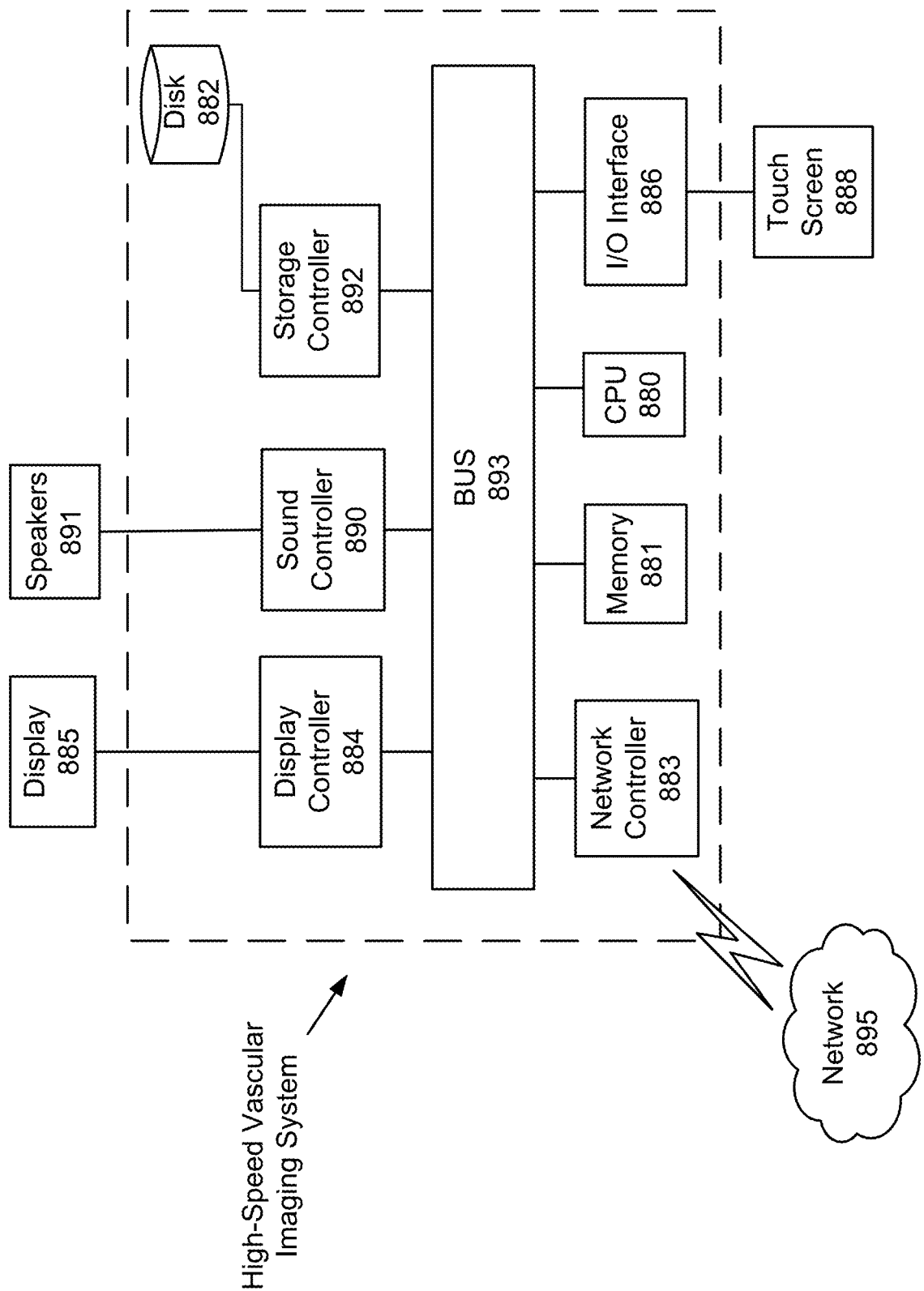
FIG. 8 is a hardware description of a high-speed vascular imaging system, according to an exemplary embodiment of the present disclosure.

FIG. 8 provides a hardware description of a HVIS, according to exemplary embodiments of the present disclosure. In an example, FIG. 8 describes a HVIS including a single processing circuitry in communication with and controlling components of a clinical imaging system such as a bi-plane X-ray system or similar. In another example, FIG. 8 describes a HVIS having multiple processing circuitries. Each of the 'modules' described above, for synchronization, evaluation, and the like, may be performed by one or more processing circuitries of the hardware description of the HVIS of FIG. 8, as appropriate. In each of the non-limiting examples described above, the display may provide graphical representations of a vascular tree and fluid flow therein and/or may be an interactive display. Though the hardware description herein is not exhaustive, it can be appreciated that the hardware description enables a variety of computer tasks including communication and control of a clinical imaging system for imaging a vascular region of interest.

In FIG. 8, the HVIS includes a CPU 880 which performs the processes described above/below. The process data and instructions may be stored in memory 881. These processes and instructions may also be stored on a storage medium disk 882 such as a hard drive (HDD) or portable storage medium or may be stored remotely. Further, the claimed advancements are not limited by the form of the computer-readable media on which the instructions of the inventive process are stored. For example, the instructions may be stored on CDs, DVDs, in FLASH memory, RAM, ROM, PROM, EPROM, EEPROM, hard disk or any other information processing device with which the HVIS communicates, such as a server or computer.

Further, the claimed advancements may be provided as a utility application, background daemon, or component of an operating system, or combination thereof, executing in conjunction with CPU 880 and an operating system such as Microsoft Windows 7, UNIX, Solaris, LINUX, Apple MAC-OS and other systems known to those skilled in the art.

The hardware elements in order to achieve the HVIS may be realized by various circuitry elements, known to those skilled in the art. For example, CPU 880 may be a specially-programmed Xenon or Core processor from Intel of America or an Opteron processor from AMD of America, or may be other processor types that would be recognized by one of ordinary skill in the art. For instance, the CPU 880 may be an Arm® Cortex®-M processor. Alternatively, the CPU 880 may be implemented on an FPGA, ASIC, PLD or using discrete logic circuits, as one of ordinary skill in the art would recognize. Further, CPU 880 may be implemented as multiple processors cooperatively working in parallel to perform the instructions of the inventive processes described above.

The HVIS in FIG. 8 also includes a network controller 883, such as an Intel Ethernet PRO network interface card from Intel Corporation of America, for interfacing with network 895. As can be appreciated, the network 895 can be a public network, such as the Internet, or a private network such as an LAN or WAN network, or any combination thereof and can also include PSTN or ISDN sub-networks. The network 895 can be wired, such as via an Ethernet network, or can be wireless, such as via a cellular network including EDGE, 3G, 4G, and 5G wireless cellular systems. The wireless network can also be WiFi, Bluetooth, near field communication, radio frequency identification device, or any other wireless form of communication that is known.

The HVIS further includes a display controller 884, such as a NVIDIA GeForce GTX or Quadro graphics adaptor from NVIDIA Corporation of America for interfacing with a display 885, such as a Hewlett Packard HPL2445w LCD monitor.

According to an embodiment, a general purpose I/O interface 886 interfaces the touch screen 888 on or separate from display 885. In an embodiment, the touch screen 888 may be implemented via capacitive sensor, resistive sensor, and the like.

It can be appreciated that the general purpose I/O interface 886 may be configured to be a special purpose I/O interface for communication with and control of one or more features of the HVIS. The one or more features can include, among others, image sensors (e.g. cameras, photon detectors, etc.) and medical equipment within the operating suite (e.g., electrocardiogram).

A sound controller 890 is also provided in the HVIS, such as Sound Blaster X-Fi Titanium from Creative, to interface with speakers/microphone 891, thereby providing sounds and/or music.

The general purpose storage controller 892 connects the storage medium disk 882 with communication bus 893, which may be an ISA, EISA, VESA, PCI, or similar, for interconnecting all of the components of the HVIS. A description of the general features and functionality of the display 885 as well as the display controller 884, storage controller 892, network controller 883, sound controller 890, and general purpose I/O interface 886 is omitted herein for brevity as these features are known.

Figure 9:
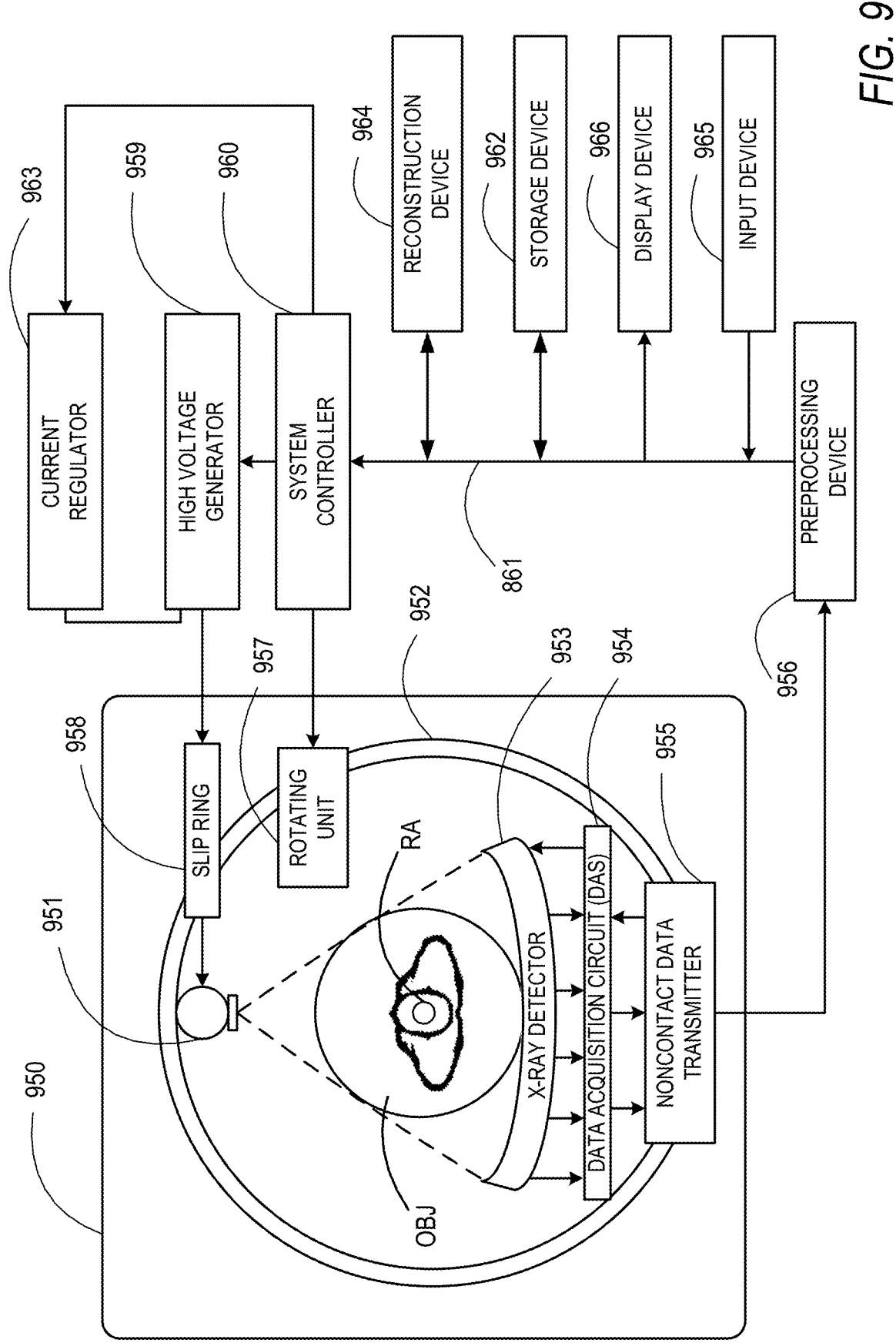
FIG. 9 is a hardware description of an imaging system of a high-speed vascular imaging system, according to an exemplary embodiment of the present disclosure.

FIG. 9 illustrates an implementation of a radiography gantry included in a CT apparatus or scanner. The radiography gantry may interface with the HVIS of FIG. 8. As shown in FIG. 9, a radiography gantry 950 is illustrated from a side view and further includes an X-ray tube 951, an annular frame 952, and a multi-row or two-dimensional-array-type X-ray detector 953. The X-ray tube 951 and X-ray detector 953 are diametrically mounted across an object OBJ on the annular frame 952, which is rotatably supported around a rotation axis RA. A rotating unit 957 rotates the annular frame 952 at a high-speed, such as 0.4 sec/rotation, while the object OBJ is being moved along the axis RA into or out of the illustrated page. The X-ray detector 953 may be a single photon X-ray detector as described above. It can be appreciated that a bi-plane detector arrangement may be configured as an extension of the set up described herein.

An embodiment of an X-ray CT apparatus according to the present inventions will be described below with reference to the views of the accompanying drawing. Note that X-ray CT apparatuses include various types of apparatuses, e.g., a rotate/rotate-type apparatus in which an X-ray tube and X-ray detector rotate together around an object to be examined, and a stationary/rotate-type apparatus in which many detection elements are arrayed in the form of a ring or plane, and only an X-ray tube rotates around an object to be examined. The present inventions can be applied to either type. In this case, the rotate/rotate-type, which is currently the mainstream, will be exemplified.

The multi-slice X-ray CT apparatus further includes a high voltage generator 959 that generates a tube voltage applied to the X-ray tube 901 through a slip ring 958 so that the X-ray tube 951 generates X-rays. The X-rays are emitted towards the object OBJ, whose cross-sectional area is represented by a circle. For example, the X-ray tube 951 having an average X-ray energy during a first scan that is less than an average X-ray energy during a second scan. Thus, two or more scans can be obtained corresponding to different X-ray energies. The X-ray detector 953 is located at an opposite side from the X-ray tube 951 across the object OBJ for detecting the emitted X-rays that have transmitted through the object OBJ. The X-ray detector 953 further includes individual detector elements or units.

The CT apparatus further includes other devices for processing the detected signals from the X-ray detector 953. A data acquisition circuit or a Data Acquisition System (DAS) 954 converts a signal output from the X-ray detector 953 for each channel into a voltage signal, amplifies he signal, and further converts the signal into a digital signal. The X-ray detector 953 and the DAS 954 are configured to handle a predetermined total number of projections per rotation (TPPR).

The above-described data is sent to a preprocessing device 956, which is housed in a console outside the radiography gantry 950 through a non-contact data transmitter 955. The preprocessing device 956 performs certain corrections, such as sensitivity correction, on the raw data. A memory 962 stores the resultant data, which is also called projection data at a stage immediately before reconstruction processing. The memory 962 is connected to a system controller 960 through a data/control bus 961, together with a reconstruction device 964, input device 965, and display 966. The system controller 960 controls a current regulator 963 that limits the current to a level sufficient for driving the CT system.

The detectors are rotated and/or fixed with respect to the patient among various generations of the CT scanner systems. In one implementation, the above-described CT system can be an example of a combined third-generation geometry and fourth-generation geometry system. In the third-generation system, the X-ray tube 951 and the X-ray detector 953 are diametrically mounted on the annular frame 952 and are rotated around the object OR as the annular frame 952 is rotated about the rotation axis RA. In the fourth-generation geometry system, the detectors are fixedly placed around the patient and an X-ray tube rotates around the patient. In an alternative embodiment, the radiography gantry 950 has multiple detectors arranged on the annular frame 952, which is supported by a C-arm and a stand.

The memory 962 can store the measurement value representative of the irradiance of the X-rays at the X-ray detector unit 953. Further, the memory 962 can store a dedicated program for executing CT image reconstruction, material decomposition, and scatter estimation and correction methods.

The reconstruction device 964 can execute the above-referenced methods. Further, reconstruction device 964 can execute pre-reconstruction processing image processing such as volume rendering processing and image difference processing as needed. The pre-reconstruction processing of the projection data performed by the preprocessing device 956 can include correcting for detector calibrations, detector nonlinearities, and polar effects, for example.

Post-reconstruction processing performed by the reconstruction device 964 can include filtering and smoothing the image, volume rendering processing, and image difference processing, as needed. The image reconstruction process can be performed using filtered back projection, iterative image reconstruction methods, or stochastic image reconstruction methods. The reconstruction device 964 can use the memory to store, e.g., projection data, training images, uncorrected images, calibration data and parameters, and computer programs.

The reconstruction device 964 can include a CPU (processing circuitry) that can be implemented as discrete logic gates, as an Application Specific Integrated Circuit (ASIC), a Field Programmable Gate Array (FPGA) or other Complex Programmable Logic Device (CPLD). An FPGA or CPLD implementation may be coded in VDHL, Verilog, or any other hardware description language and the code may be stored in an electronic memory directly within the FPGA or CPLD, or as a separate electronic memory. Further, the memory 962 can be non-volatile, such as ROM, EPROM, EEPROM or FLASH memory. The memory 962 can also be volatile, such as static or dynamic RAM, and a processor, such as a microcontroller or microprocessor, can be provided to manage the electronic memory as well as the interaction between the FPGA or CPLD and the memory.

Alternatively, the CPU in the reconstruction device 964 can execute a computer program including a set of computer-readable instructions that perform the functions described herein, the program being stored in any of the above-described non-transitory electronic memories and/or a hard disc drive, CD, DVD. FLASH drive or any other known storage media. Further, the computer-readable instructions may be provided as a utility application, background daemon, or component of an operating system, or combination thereof, executing in conjunction with a processor, such as a Xeon processor from Intel of America or an Opteron processor from AMD of America and an operating system, such as Microsoft 10, UNIX, Solaris, LINUX, Apple, MAC-OS and other operating systems known to those skilled in the art. Further, CPU can be implemented as multiple processors cooperatively working in parallel to perform the instructions.

In one implementation, the reconstructed images can be displayed on a display 966. The display 966 can be an LCD display, CRT display, plasma display, OLED, LED or any other display known in the art.

The memory 962 can be a hard disk drive, CD-ROM drive, DVD drive, FLASH drive, RAM, ROM or any other electronic storage known in the art.

According to an embodiment, a flat panel with standard TFT readout may be used at the X-ray entrance side and a very high-speed CMOS light detector may be used at the back side to share the light output from an X-ray absorbing scintillation layer. Large CMOS imaging chips are available and used in the FASTCAM line of 1000 fps cameras were the pixel size is up to 20 µm×20 µm for a 2 cm×2 cm imaging chip. Consideration will be given to estimating sensitivity, capacity, spatial resolution, pixel size, and other physical descriptors for discussions with potential manufacturers.

According to an embodiment, a single phosphor layer or a large area PC may be used and a region of interest attenuator may be used to reduce patient exposure peripheral to the region of interest. This technique can be combined with variable temporal filtering to further reduce noise in the periphery even with the reduced dose; however, because of the larger range of detector exposure times available, there will be greater flexibility and range of temporal filtering available that will be explored. Additionally, the location of the region of interest as varied during a dynamic imaging procedure with the correction mask found using a machine learning technique may be evaluated.

Various aneurysm treatment devices, such as coils and flow diverter stents, may be investigated within three-dimensional phantoms described herein. Many variables affect details of flow and contrast patterns. These include morphology or shape of vessels and pathologies, contrast delivery details including catheter features and placement, bolus timing and shape, fluid pressure differentials and cycle, fluid viscosity, and synchrony of imaging with flow as well as design of stent flow diverter or other interventional device. Rigorous study of the effect on flow patterns of each of these variables will require an extensive series of experiments to enable an understanding of the impact of detailed flow data on observer responses. Both quantitative and semi-quantitative studies are described below.

EXAMPLES

Example 1

The high-speed detector reported in this work was a direct photon counting detector (Actaeon, XCounter, Danderyd. Sweden) with 0.75 mm thick CdTe direct detection layer, dual energy thresholding, charge sharing correction, and frame rates up to 1000 fps. It has a 100 µm pixel pitch, active area of 1"×1", 256 pixels×256 pixels readout, and is capable of dual energy acquisition with two independent thresholds on each pixel.

A three-dimensional printed aneurysm phantom with flow rates and wall pressure typical to that in humans was used to simulate vascular conditions for evaluation of the high-speed X-ray detector. The aneurysm model was three-dimensional printed in house using an Object Polyjet 3D printer, Model 260V (Objet-Stratasys Inc, Eden Prairie, Minn.) with Connex 3 multi-material ink. The phantom was then taped on to a platform with provision for flow in and out. The tubes were then connected to a pulsatile pump (Easy Jet 11, Cole Parmer Inc, Vernon Hills, IL) and set to simulate the flow and wall pressure typical for humans. This setup was placed on the bottom rack of a Unistrut platform and the high-speed detector was placed on the top rack with a geometric magnification of 1.1× at the detector surface. After collimating X-rays to the field of view of the high-speed detector, a radiographic protocol from a Canon-Toshiba Surginix SXT 2000A Mobile C-Arm system was used. The technique parameters were set at 70 kVp, 100 mA, 3s with an added filtration of 2.55 mm Al. The exposure at the detector surface per frame for 1000 fps was 470 pR/frame. The Actaeon imaging mode was "high sensitivity" with anti-coincidence turned on. Imaging mode has a built in anti-charge sharing correction. The thresholds were fixed at 20 keV and 34 keV such that the first threshold was above the instrumentation noise and the second one was above the K absorption edge of iodine contrast used in the study. Once the "blood" in the flow loop was set into motion, various delivery catheters were inserted into the vessel through an introducer, with the nozzle of the catheter being placed at three locations proximal to the aneurysm model. The delivery catheters used were Neuron Model 6F 070 (Penumbra Inc., Alameda, Calif.), Envoy XB 6F MPC (Codman Neuro Inc., New Brunswick. N.J.), Siteseer Cardiac 6F A-2 (Medtronic Inc., Fridley, Minn.) and Chaperon 6F inner catheter (Microvention Terumo Inc., Aliso Viejo, Calif.). All of the delivery catheters had multi-purpose angled nozzles. Iodine contrast (Omnipaque, 350 mgI/mL, GE Healthcare, Chicago, IL) was injected through the delivery catheter with gas bubbles introduced during a subset of runs using an auto injector (Medrad PPD11060507, Medrad Inc., Warrendale, PA). Flow was monitored at 1000 fps and 1200 images were acquired for every run. For a consistent volume of 10 ml, injection rates were varied from 10 mL/s to 30 mL/s. Radiographic exposures and contrast injections were triggered at three different delay settings so as to get the leading edge, vortex formation and trailing end of the flow.

For quantitative measurements including velocity of the flow at various stages, two sequential images were selected. The location of a moving contrast wave front was measured by number of pixels using ImageJ and the same wave front was tracked and the position recorded in pixels in the subsequent image. The Euclidean distance was measured using the distance formula understanding a temporal resolution of 1 ms. Accordingly, the velocity could be calculated at various locations of the contrast wave front using the formula given below:

$$v = \frac{\sqrt{(X_f - X_i)^2 + (Y_f - Y_i)^2}}{1 \text{ ms}} * 100 \text{ µm},$$

Alternate measurements of velocity were achieved using a temporally subtracted sequence. This includes, for a collection of moving dark pixels corresponding to a contrast wave front, measuring the width across in pixels which can be translated to velocity.

Figure 10:
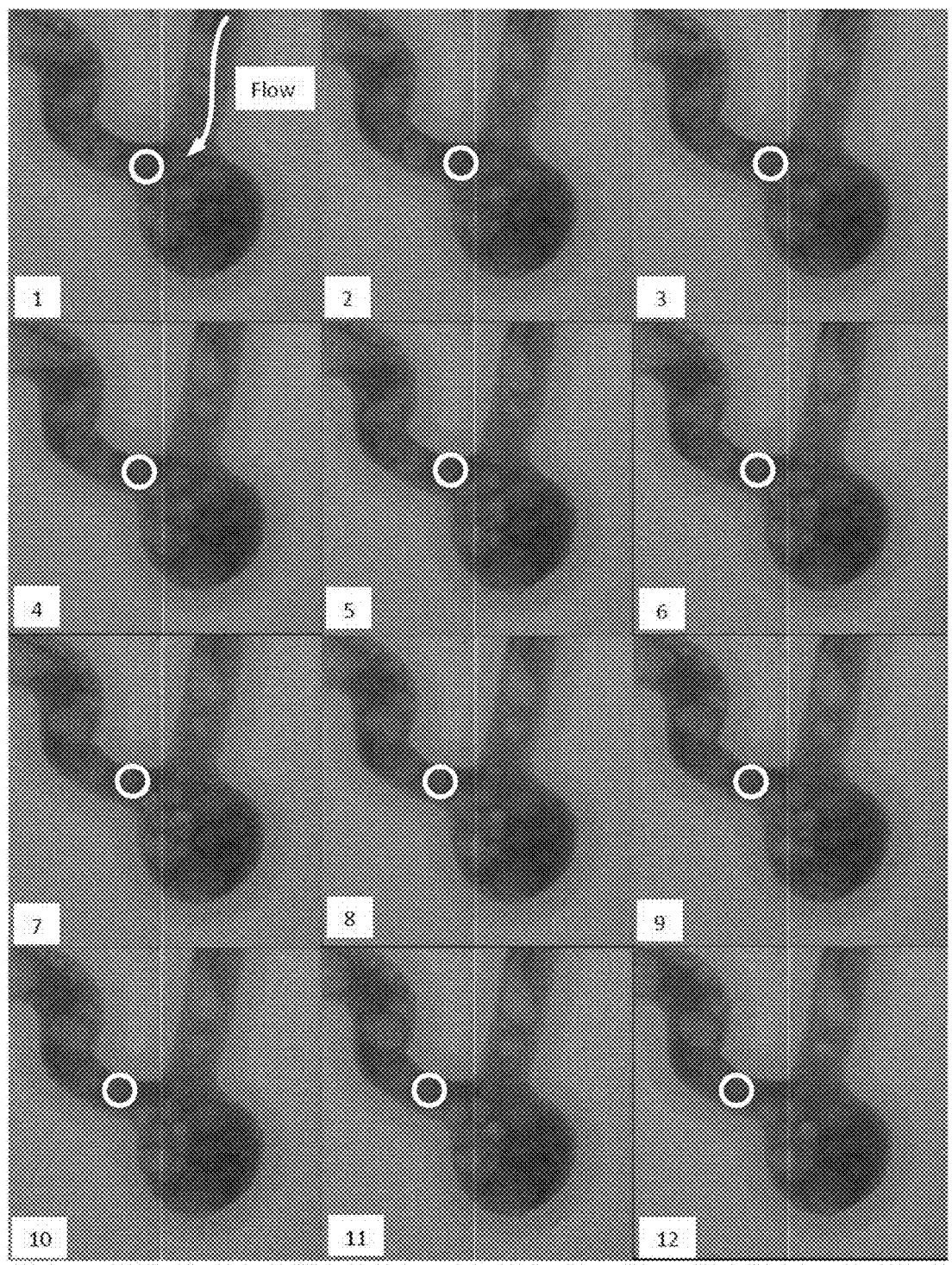
FIG. 10 is a sequence of images of contrast agent within an aneurysm phantom, according to an exemplary embodiment of the present disclosure.

FIG. 10 is a panel of twelve images acquired over a 1.2 second period of time, progressing from left to right and top to bottom. The images illustrate an example in which contrast was injected into the vessel with air to produce bubbles that could be tracked to observe the path of contrast flow and to measure velocities. Flow follows the path indicated by the white arrow. By tracking the change in position of the center of one of the produced bubbles, such as the bubble within the white circle of each image, it was found that the average blood velocity was 27 cm/s in the model phantom.

Figure 11B:
FIG. 11B is a simulated image of contrast agent within an aneurysm phantom.
Figure 11A:
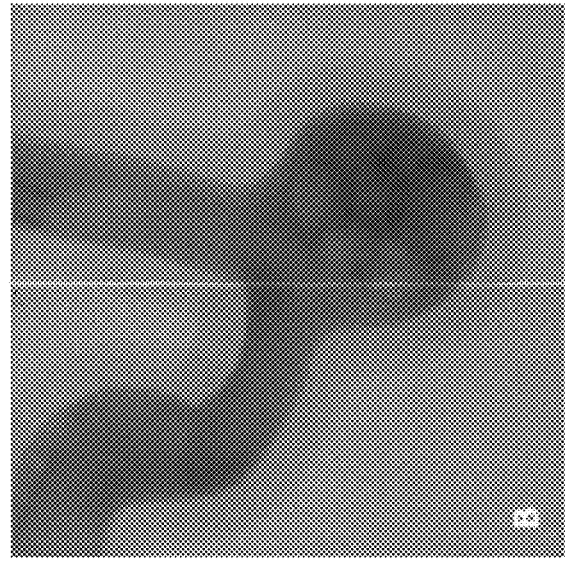
FIG. 11A is a simulated image of contrast agent within an aneurysm phantom.

With reference to FIG. 11A and FIG. 11B, and in order to compare the detail visible above with conventional angiograms, FIG. 11A and FIG. 11B are simulations from the sequence of FIG. 10 but as an integration over twelve consecutive frames in order to simulate a pulse width of 12 ms (FIG. 11A) and a continuous fluoroscopic acquisition using 30 fps (FIG. 11B). As viewed in FIG. 11A and FIG. 11B, it can be observed that the bubbles that were used to measure blood velocity in the artery are substantially blurred.

Figure 12C:
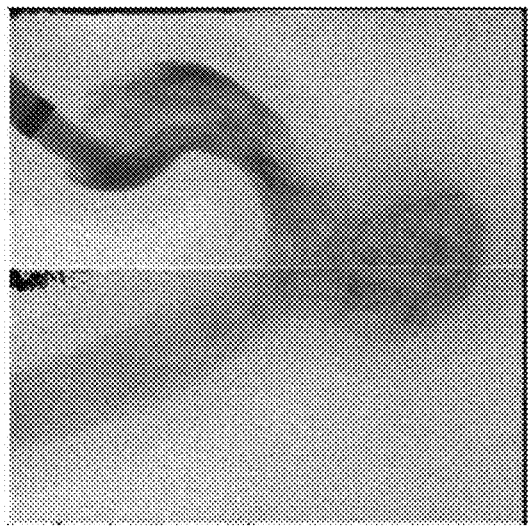
FIG. 12C is one of a series of images of contrast agent within an aneurysm phantom, according to an exemplary embodiment of the present disclosure.
Figure 12B:
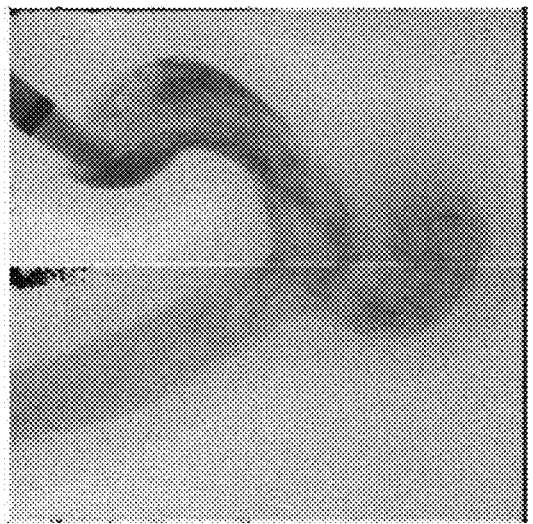
FIG. 12B is one of a series of images of contrast agent within an aneurysm phantom, according to an exemplary embodiment of the present disclosure.
Figure 12A:
FIG. 12A is one of a series of images of contrast agent within an aneurysm phantom, according to an exemplary embodiment of the present disclosure.
Figure 13C:
FIG. 13C is one of a series of images of contrast agent within an aneurysm phantom after a flow diverter is deployed, according to an exemplary embodiment of the present disclosure.
Figure 13B:
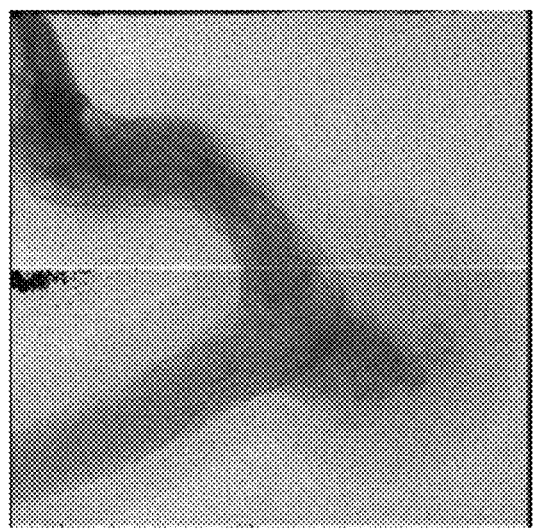
FIG. 13B is one of a series of images of contrast agent within an aneurysm phantom after a flow diverter is deployed, according to an exemplary embodiment of the present disclosure.
Figure 13A:
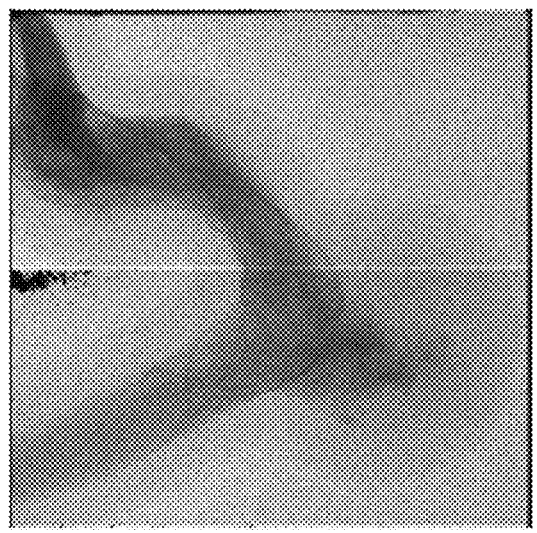
FIG. 13A is one of a series of images of contrast agent within an aneurysm phantom after a flow diverter is deployed, according to an exemplary embodiment of the present disclosure.
Figure 14A:
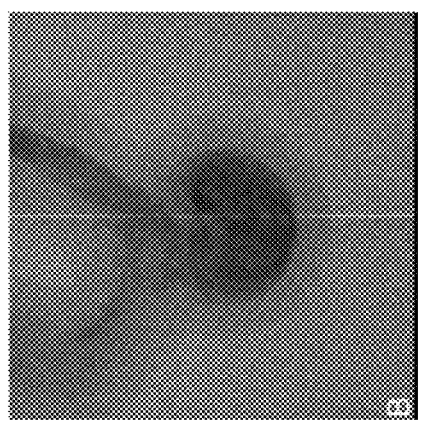
FIG. 14A is one of a series of images of contrast agent within an internal carotid artery aneurysm model before a flow diverter is deployed, according to an exemplary embodiment of the present disclosure.
Figure 14B:
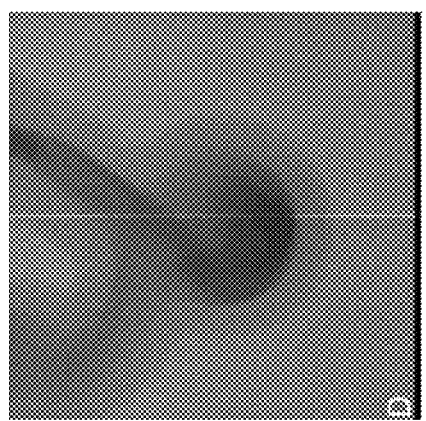
FIG. 14B is one of a series of images of contrast agent within an internal carotid artery aneurysm model before a flow diverter is deployed, according to an exemplary embodiment of the present disclosure.
Figure 14C:
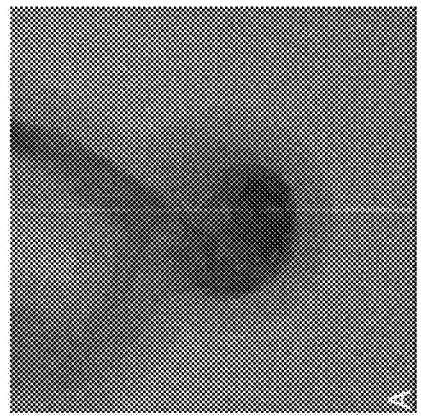
FIG. 14C is one of a series of images of contrast agent within an internal carotid artery aneurysm model before a flow diverter is deployed, according to an exemplary embodiment of the present disclosure.
Figure 14D:
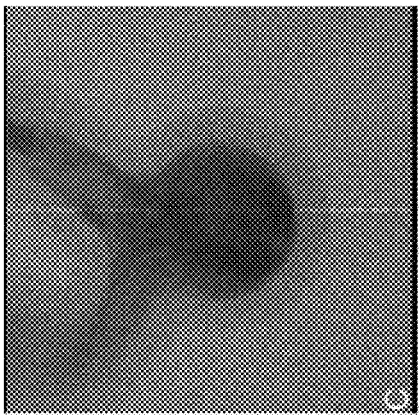
FIG. 14D is an average of a series of images of contrast agent within an internal carotid artery aneurysm model before a flow diverter is deployed, according to an exemplary embodiment of the present disclosure.
Figure 15A:
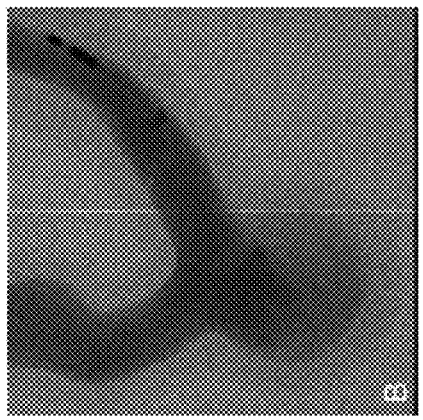
FIG. 15A is one of a series of images of contrast agent within an internal carotid artery aneurysm model after a flow diverter is deployed, according to an exemplary embodiment of the present disclosure.
Figure 15B:
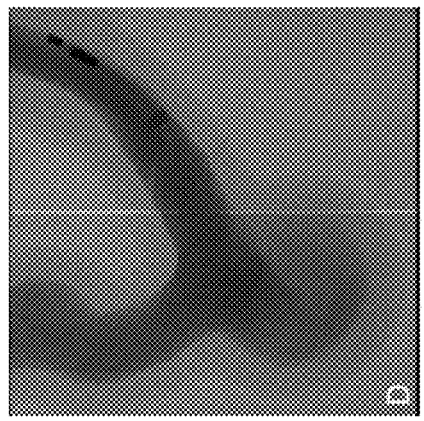
FIG. 15B is one of a series of images of contrast agent within an internal carotid artery aneurysm model after a flow diverter is deployed, according to an exemplary embodiment of the present disclosure.
Figure 15C:
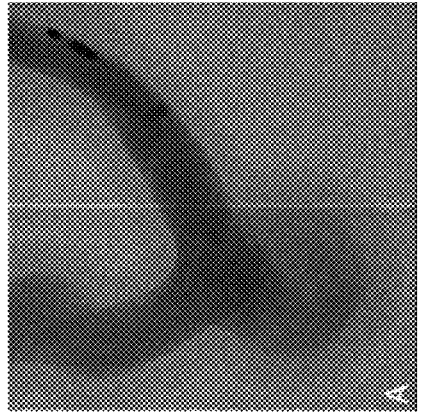
FIG. 15C is one of a series of images of contrast agent within an internal carotid artery aneurysm model after a flow diverter is deployed, according to an exemplary embodiment of the present disclosure.
Figure 15D:
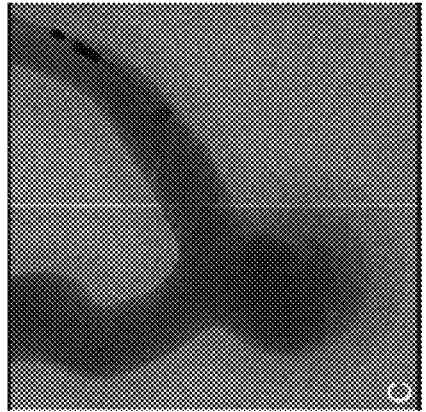
FIG. 15D is an average of a series of images of contrast agent within an internal carotid artery aneurysm model after a flow diverter is deployed, according to an exemplary embodiment of the present disclosure.

Another set of high-speed sequences comparing iodine contrast injections were taken of an aneurysm phantom before and after a flow diverter, or stent, was deployed. FIG. 12A, FIG. 12B, and FIG. 12C demonstrate development of contrast vortices in the aneurysm sac when no flow diverter is present in the aneurysm phantom. Alternatively, FIG. 13A, FIG. 13B, and FIG. 13C demonstrate disruption of the vortex due to the placement of a flow diverter, or pipeline stent, across the neck of the aneurysm. In the selected individual images from the high-speed sequences, shown in FIG. 12A through FIG. 13C, changes in flow patterns in an aneurysm phantom before and after intervention can be appreciated through use of high-speed image acquisitions.

As seen in the series of high-speed image acquisitions with reduced detector exposure durations, more flow details are visible. With regard to FIG. 1, visible gas bubbles within iodine contrast media completely fill the vessel. The gas bubbles can show the detailed flow pattern as they move across the field of view. Flow rates or velocities can be calculated with these bubbles as markers, knowing the time separation. In an embodiment, a high temporal resolution of 1 ms may be used. The vertical line in the center of the images, due to the modular design of the Actaeon high-speed detector, can be used as a reference marker when following an individual bubble. In the sequential flow of FIG. 1, the average blood velocity was estimated to be 27 cm/s.

With regard to FIG. 11A through FIG. 13C, the contrast medium was initialing entering the aneurysm phantom so that individual streams could be followed prior to the complete filling of the aneurysm phantom. Under the different conditions of no flow diverter (FIG. 12A, FIG. 12B, and FIG. 12C) compared to with a flow diverter (FIG. 13A, FIG. 13B, and FIG. 13C), the effect on detailed flow visualization was to provide a blurred (i.e., degraded) image when conventional angiographic settings were simulated. When 1000 fps acquisition was used the detailed flow patterns including the effect on the vortex patterns when a stent was deployed became clearly visualized.

Example 2

The high-speed detector used herein is an Actaeon detector (XCounter, Danderyd, Sweden). The Actaeon detector is a single photon-counting direct CaTe detector with a 100 pp pitch and a 256×256 matrix size capable of acquisition speeds up to 1000 fps.

Three-dimensional printed models simulating an internal carotid artery aneurysm were connected to a pulsatile flow loop with water used as the circulating fluid. A 21-mm aluminum block was added underneath the model to approximate the X-ray attenuation of a human head (RQA5 attenuator, IEC 61267-1, 62220-1).

The high-speed detector was mounted on a Unistrut platform (Unistrut, Harvey, Illinois) and positioned 6 cm above the phantom, resulting in a magnification factor of 1.08, and was set to acquire continuously at 1000 fps. An Infinix biplane C-arm system (Model INFX-8000V; Canon, Otawara, Japan) was used as the X-ray source. Peak tube voltage was set to 92 kV, the tube current was set to 160 mA, and the exposure pulse width was set to 100 ms with a medium focal spot. A 6F catheter (Model 7512-23; Merit Medical, South Jordan, Utah) was placed proximal to the aneurysm region. With the catheter in place, an AutoSyringe (Model PPD11060507; Medrad, Warrendale, Pennsylvania) was used to inject a 10-mL burst of 350 mg of undiluted iodine per milliliter of contrast agent into the 3D printed vessel at 10 mL/s. The delay between the injection and the X-ray trigger was varied to observe contrast flow variation at different time intervals post injection. Images of contrast flow before and after deployment of a pipeline embolization device (PED) were acquired. The PED was partially deployed, resulting in complete coverage of the aneurysmal ostia to accommodate multiple experiments. Images were acquired at 1000 fps, yielding 100 images for every 100 ms X-ray exposure period. For comparison with conventional angiography, 40 of these frames were averaged to simulate 1 image acquired with an exposure pulse width of 40 ms.

The air kerma at the phantom entrance surface was measured using a 6-mL PTW ionization chamber and electrometer (Model T10023 Unidos; PTW, Freiburg. Germany). The air kerma per frame was 12.3 µGy at the phantom entrance surface for each of the 1 ms images acquired at 1000 fps. The air kerma for frames integrated over a sequence of 100 ms was 1.23 mGy at the entrance surface. This is approximately the dose expected from a DSA run containing 20 frames.

With reference now to FIG. 14A through FIG. 14D, digital subtraction angiography (DSA) images show flow detail in an internal carotid artery aneurysm model when no PED flow diverter is deployed. Images were acquired at 1000 fps and separated by 25 frames each, for FIG. 14A, FIG. 14B, and FIG. 14C, with a single average image of one 40 ms X-ray pulse comprising FIG. 14D. The vertical line shows the 1-pixel boundary between detector modules. As shown, FIG. 14D includes the same sequence as FIG. 14A through FIG. 14C but with reduced noise and increased motion blurring. The blur for an actual DSA frame will depend on the pulse width used and the velocity of the blood flow. Noise reduction and blurring over a few tens of a millisecond pulse width would correspond to those of a standard angiography frame.

With reference now to FIG. 15A through FIG. 15D, DSA images shown flow detail in an internal carotid artery aneurysm model when a PED flow diverter is partially deployed. Compared with standard angiographic images, FIG. 14A through FIG. 14C and FIG. 15A through FIG. 15C demonstrate that additional information, such as detailed flow patterns in the aneurysm region, can be visualized in images acquired at 1000 fps due to higher temporal resolution. For instance, when no PED flow diverter is deployed, images acquired at 1000 fps (e.g., FIG. 14A through FIG. 14C) clearly show flow into the aneurysm with the development of vortices of contrast in the aneurysmal sac. Alternatively, images acquired with a PED flow diverter in place (e.g., FIG. 15A through FIG. 15C) show more diffuse flow of contrast into the aneurysm with lower apparent flow velocities and delayed development of vortices in the aneurysm sac. As demonstrated in the flow phantoms of the present study, changes in contrast media streamlines and blob shapes could easily be seen with 1 ms frame intervals.

High-speed imaging, enabled by this new detector, allows clinicians to observe detailed flow patterns in the 3D-printed phantom, including differentiation of flow patterns into the target aneurysm versus the parent vessel. These gains in temporal information could potentially impact treatment decisions by allowing clinicians to assess flow patterns in real-time during a procedure. During treatment, clinicians assess the adequacy of stent placement by looking for indirect signs of flow diversion, such as evaluating wall apposition and looking for contrast stasis within the aneurysm sac. Detailed visualization of changes in flow dynamics could allow clinicians to directly assess factors that have been shown to improve the efficacy of flow diverters, such as decreases in flow vortices.

Other potential clinical uses include the detection of endoleaks near an aneurysm, identification of residual flow that could cause an aneurysm to regrow, blood impingement patterns that could lead to coil compaction, and diversion of jets into an aneurysm at locations where flow may be less intuitive (such as at a bifurcation).

The imager described here is a small-FOV, ROI detector. It is contemplated that within a system that also provides a conventional full FOV capability, a high-speed unit somewhat larger than that shown here could be deployed during an interventional procedure.

Improvements in spatial and temporal resolution of angiography have the potential to significantly improve outcomes by giving clinicians additional real-time insights into the details of flow dynamics, which allow intraoperative modifications to improve procedural safety and long-term efficacy.

Obviously, numerous modifications and variations are possible in light of the above teachings. It is therefore to be understood that within the scope of the appended claims, the invention may be practiced otherwise than as specifically described herein.

Embodiments of the present disclosure may also be as set forth in the following parentheticals.

(1) A method of determining dynamic vascular parameters of blood flow, comprising acquiring two-dimensional projection images of a vascular region of interest at a predetermined frequency, the vascular region of interest being downstream of a site of vascular administration of a radio-opaque medium, identifying, within the acquired two-dimensional projection images, heterogeneities of the radio-opaque medium, and determining, by processing circuitry, the dynamic vascular parameters of the blood flow based on spatial movements of the identified heterogeneities of the radio-opaque medium.

(2) The method of (1), further comprising determining timing of a cardiac cycle of a patient based on a cardiac signal of the patient, synchronizing the vascular administration of the radio-opaque medium with the determined timing of the cardiac cycle, and synchronizing the acquiring the two-dimensional projection images of the vascular region of interest with the determined timing of the cardiac cycle.

(3) The method of either (1) or (2), further comprising synchronizing generation of radiation with the determined timing of the cardiac cycle.

(4) The method of any one of (1) to (3), wherein the vascular administration of the radio-opaque medium is temporally discontinuous.

(5) The method of any one of (1) to (4), wherein the temporally discontinuous vascular administration of the radio-opaque medium includes administration of variable quantities of the radio-opaque medium.

(6) The method of any one of (1) to (5), wherein the determined timing of the cardiac cycle is based on a phase of the cardiac cycle.

(7) The method of any one of (1) to (6), wherein the predetermined frequency is greater than 100 Hz.

(8) The method of any one of (1) to (7), wherein the acquiring acquires the two-dimensional projection images of the vascular region of interest as a series of sequential two-dimensional projection images.

(9) The method of any one of (1) to (8), wherein the dynamic vascular parameters of the blood flow include streamlines and velocity distributions.

(10) The method of any one of (1) to (9), wherein the heterogeneities of the radio-opaque medium are spherical particles.

(11) The method of any one of (1) to (10), wherein the heterogeneities of the radio-opaque medium are biodegradable.

(12) The method of any one of (1) to (11), wherein the acquiring acquires the two-dimensional projection images of the vascular region of interest via biplane radiation detectors.

(13) The method of any one of (1) to (12), wherein the synchronizing the vascular administration of the radio-opaque medium and the synchronizing the acquiring of the two-dimensional projection images include a time delay based on the determined timing of the cardiac cycle.

(14) The method of any one of (1) to (13), wherein the cardiac signal of the patient is received from an electrocardiogram.

(15) An apparatus for determining dynamic vascular parameters of blood flow, comprising processing circuitry configured to acquire two-dimensional projection images of a vascular region of interest at a predetermined frequency, the vascular region of interest being downstream of a site of vascular administration of a radio-opaque medium, identify heterogeneities of the radio-opaque medium within the acquired two-dimensional projection images, and determine the dynamic vascular parameters of the blood flow based on spatial movements of the identified heterogeneities of the radio-opaque medium.

(16) The apparatus of (15), wherein the processing circuitry is further configured to determine timing of a cardiac cycle of a patient based on a cardiac signal of the patient, synchronize the vascular administration of the radio-opaque medium with the determined timing of the cardiac cycle, and synchronize the acquiring the two-dimensional projection images of the vascular region of interest with the determined timing of the cardiac cycle.

(17) The apparatus of either (15) or (16), wherein the vascular administration of the radio-opaque medium is temporally discontinuous.

(18) The apparatus of any one of (15) to (17), wherein the temporally discontinuous vascular administration of the radio-opaque medium includes administration of variable quantities of the radio-opaque medium.

(19) The apparatus of any one of (15) to (18), wherein the predetermined frequency is greater than 100 Hz.

(20) The apparatus of any one of (15) to (19), wherein the dynamic vascular parameters of the blood flow include streamlines and velocity distributions.

Thus, the foregoing discussion discloses and describes merely exemplary embodiments of the present invention. As will be understood by those skilled in the art, the present invention may be embodied in other specific forms without departing from the spirit or essential characteristics thereof. Accordingly, the disclosure of the present invention is intended to be illustrative, but not limiting of the scope of the invention, as well as other claims. The disclosure, including any readily discernible variants of the teachings herein, defines, in part, the scope of the foregoing claim terminology such that no inventive subject matter is dedicated to the public.

The invention claimed is:

1. A method of determining dynamic vascular parameters of blood flow, comprising:
   acquiring two-dimensional projection images of a vascular region of interest at a predetermined frequency, the vascular region of interest being downstream of a site of vascular administration of a radio-opaque medium;
   identifying, within the acquired two-dimensional projection images, heterogeneities of the radio-opaque medium, the heterogeneities being generated by the vascular administration of the radio-opaque medium that is temporally discontinuous with high frequency provided by a rotary peristaltic pump; and
   tracking, by processing circuitry, a change in position of the heterogeneities within the vascular region of interest, based on the position where a region of particles of the radio-opaque medium is present in the two-dimensional projection images in which the heterogeneities are identified, and determining the dynamic vascular parameters of the blood flow based on the change in position of the tracked heterogeneities of the radio-opaque medium.

2. The method of claim 1, further comprising
   determining timing of a cardiac cycle of a patient based on a cardiac signal of the patient,
   synchronizing the vascular administration of the radio-opaque medium with the determined timing of the cardiac cycle, and
   synchronizing the acquiring the two-dimensional projection images of the vascular region of interest with the determined timing of the cardiac cycle.

3. The method of claim 2, further comprising synchronizing generation of radiation with the determined timing of the cardiac cycle.

4. The method of claim 1, wherein the temporally discontinuous vascular administration of the radio-opaque medium includes administration of variable quantities of the radio-opaque medium.

5. The method of claim 2, wherein the determined timing of the cardiac cycle is based on a phase of the cardiac cycle.

6. The method of claim 1, wherein the predetermined frequency is greater than 100 Hz.

7. The method of claim 1, wherein the acquiring acquires the two-dimensional projection images of the vascular region of interest as a series of sequential two-dimensional projection images.

8. The method of claim 1, wherein the dynamic vascular parameters of the blood flow include streamlines and velocity distributions.

9. The method of claim 1, wherein the acquiring acquires the two-dimensional projection images of the vascular region of interest via biplane radiation detectors.

10. The method of claim 2, wherein the synchronizing the vascular administration of the radio-opaque medium and the synchronizing the acquiring of the two-dimensional projection images include a time delay based on the determined timing of the cardiac cycle.

11. The method of claim 2, wherein the cardiac signal of the patient is received from an electrocardiogram.

12. An apparatus for determining dynamic vascular parameters of blood flow, comprising:
    processing circuitry configured to
      acquire two-dimensional projection images of a vascular region of interest at a predetermined frequency, the vascular region of interest being downstream of a site of vascular administration of a radio-opaque medium,
      identify heterogeneities of the radio-opaque medium within the acquired two-dimensional projection images, the heterogeneities being generated by the vascular administration of the radio-opaque medium that is temporally discontinuous with high frequency provided by a rotary peristaltic pump, and
      track a change in position of the heterogeneities within the vascular region of interest, based on the position where a region of particles of the radio-opaque medium is present in the two-dimensional projection images in which the heterogeneities are identified, and determine the dynamic vascular parameters of the blood flow based on the change in position of the tracked heterogeneities of the radio-opaque medium.

13. The apparatus of claim 12, wherein the processing circuitry is further configured to
    determine timing of a cardiac cycle of a patient based on a cardiac signal of the patient,
    synchronize the vascular administration of the radio-opaque medium with the determined timing of the cardiac cycle, and
    synchronize the acquiring the two-dimensional projection images of the vascular region of interest with the determined timing of the cardiac cycle.

14. The apparatus of claim 12, wherein the temporally discontinuous vascular administration of the radio-opaque medium includes administration of variable quantities of the radio-opaque medium.

15. The apparatus of claim 12, wherein the predetermined frequency is greater than 100 Hz.

16. The apparatus of claim 12, wherein the dynamic vascular parameters of the blood flow include streamlines and velocity distributions.

17. The method of claim 1, wherein the vascular administration of the radio-opaque medium is temporally discontinuous with a frequency range of between 5 Hz and 20 Hz.

* * * * *